US007435797B2

(12) United States Patent
Lowman et al.

(10) Patent No.: US 7,435,797 B2
(45) Date of Patent: Oct. 14, 2008

(54) ANTI-HER2 ANTIBODY VARIANTS

(75) Inventors: Henry B. Lowman, El Granada, CA (US); Resi B. Gerstner, Burlingame, CA (US); Paul J. Carter, Mercer Island, WA (US)

(73) Assignee: Genentech, Inc., South San Francisco, CA (US)

( * ) Notice: Subject to any disclaimer, the term of this patent is extended or adjusted under 35 U.S.C. 154(b) by 608 days.

(21) Appl. No.: 10/410,894

(22) Filed: Apr. 9, 2003

(65) Prior Publication Data

US 2003/0228663 A1 Dec. 11, 2003

Related U.S. Application Data

(60) Provisional application No. 60/371,609, filed on Apr. 10, 2002.

(51) Int. Cl.
C07K 16/00 (2006.01)
C12P 21/08 (2006.01)
(52) U.S. Cl. .............. 530/387.3; 530/387.5; 530/387.7; 530/388.85; 424/133.1; 424/141.1; 424/143.1; 424/156.1; 435/69.6
(58) Field of Classification Search .............. 530/387.3, 530/350, 388.2, 326, 300, 387.1, 387.5, 387.7; 424/133.1, 130.1, 143.1, 277.1
See application file for complete search history.

(56) References Cited

U.S. PATENT DOCUMENTS

| | | | | |
|---|---|---|---|---|
| 4,968,603 | A | 11/1990 | Slamon et al. | 435/6 |
| 5,677,171 | A | 10/1997 | Hudziak et al. | 435/240.27 |
| 5,783,186 | A | 7/1998 | Arakawa et al. | 424/413.1 |
| 5,821,337 | A | 10/1998 | Carter et al. | 530/387.3 |
| 5,824,311 | A | 10/1998 | Greene et al. | 424/138.1 |
| 5,837,234 | A | 11/1998 | Gentile et al. | 424/93.7 |
| 2002/0035736 | A1 | 3/2002 | Erickson et al. | 800/14 |

FOREIGN PATENT DOCUMENTS

| | | |
|---|---|---|
| WO | WO 92/20798 | 11/1992 |
| WO | WO 92/22653 | 12/1992 |
| WO | WO 93/21319 | 10/1993 |
| WO | WO 94/00136 | 1/1994 |
| WO | WO 94/22478 | 10/1994 |
| WO | WO 96/16673 | 6/1996 |
| WO | WO 03/068801 | 8/2003 |

OTHER PUBLICATIONS

Rudikoff et al (Proc. Natl. Acad. Sci. USA 1982 vol. 79 p. 1979.*
(Paul, Fundamental Immunology, 3rd Edition, 1993, pp. 292-295, under the heading "Fv Structure and Diversity in Three Dimensions").*
Rudikoff et al (Proc. Natl. Acad. Sci. USA, 79:1979-1983, Mar. 1982).*
Casset et al. ((2003) BBRC 307, 198-205).*
Burgess et al, Journal of Cell Biology vol. 111 Nov. 1990 2129-2138.*
Lazar et al Molecular and Cellular Biology Mar. 1988 vol. 8 No. 3 1247-1252.*
Colman et al (Research in Immunology 1994, 145:33-36).*
Ibragimova and Eade (Biophysical Journal, Oct. 1999, vol. 77, pp. 2191-2198).*
Bendig M. M. 1995. Methods: A Companion to Methods in Enzymology, 8:83-93.*
Aasland et al., "Expression of oncogenes in thyroid tumours: coexpression of c-$erbB2/neu$ and c-$erbB$", $Br. J. Cancer$, 57:358-363 (1988).
Arteaga et al., "p185$^{c\text{-}erbB\text{-}2}$ signaling enhances cisplatin-induced cytotoxicity in human breat carcinoma cells: association between an oncogenic receptor tyrosine kinase and drug-induced DNA repair", $Cancer Res.$, 54:3758-3765 (1994).
Bacus et al., "Differentiation of cultured human breast cancer cells (AU-565 and MCF-7) associated with loss of cell surface HER-2/$neu$ antigen", $Molecular Carcinogenesis$, 3:350-362 (1990).
Bacus et al., "Tumor-inhibitory monoclonal antibodies to the HER-2/neu receptor induce differentiation of human breast cancer cells", $Cancer Research$, 52:2580-2589 (1992).
Borst et al., "Oncongene alterations in endometrial carcinoma", $Gynecol. Oncol.$, 38:364-366 (1990).
Carter et al., "Humanization of an anti-p185$^{HER2}$ antibody for human cancer therapy", $Proc. Nat. Acad. Sci. USA$ 89: 4285-4289 (1992).
Chothia et al., "Conformations of immunoglobulin hypervariable regions", $Nature$, 342(6252):877-83 (1989).
Cobleigh et al., "Multinational study of the efficacy and safety of humanized anti-HER2 monoclonal antibody in women who have HER2-overexpressing metastatic breast cancer that has progressed after chemotherapy for metastic disease", $J Clin. Oncol.$, 17:2639-2648 (1999).
Cohen et al., "Expression pattern of the $neu$ (NGL) gene-encoded growth factor receptor protein (p185$neu$) in normal and transformed epithelial tissues of the digestive tract," $Oncogene$, 4:81-88 (1989).
D'souza et al., "Overexpression of ERBB2 in human mammary epithelial cells signals inhibition of transcription of the E-cadherin gene", $Proc. Natl. Acad. Sci.$, 91:7202-7206 (1994).
Drebin et al., "Down-modulation of an oncogene protein product and reversion of the transformed phenotype by monoclonal antibodies", $Cell$, 41:695-706 (1985).
Drebin et al., "Monoclonal antibodies reactive with distinct domains of the $neu$ oncongene-encoded p185 molecule exert synergistic anti-tumor effects in vivo", $Oncogene$, 2:273-277 (1988).
Eigenbrot et al., "X-ray structures of the antigen-binding domains from three variants of humanized anti-p185$^{HER2}$ antibody 4D5 and comparison with molecular modeling", $J Mol Bio$, 229(4):969-95 (1993).
Fendly et al., "Characterization of murine monoclonal antibodies reactive to either the human epidermal growth factor receptor or HER2/$neu$ gene product", $Cancer Res.$, 50(5):1550-8 (1990).

(Continued)

$Primary Examiner$—David J. Blanchard
(74) $Attorney, Agent, or Firm$—Atulya R. Agarwal; Ginger R. Dreger, Esq.; Goodwin Procter LLP

(57) ABSTRACT

The present invention concerns novel antibody variants, particularly anti-HER2 antibody variants having substitutions at positions within the variable domains of the heavy and light chains

30 Claims, 8 Drawing Sheets

OTHER PUBLICATIONS

Fukushigi et al., "Localization of a novel v-*erb*B-related gene, c-*erb*B-2, on human chromosome 17 and its amplification in a gastric cancer cell line", *Mol Cell Biol.*, 6:955-958 (1986).
Gallivan, J. P. & Dougherty, D. A., "Cation-π interactions in structural biology", *Proc Natl. Acad. Sci. USA*, 96(17):9459-64 (1999).
Gu et al., "Overexpression of her-2/*neu* in human prostate cancer and benign hyperplasia", *Cancer Lett.*, 99:185-9 (1996).
Geurin et al., "Overexpression of either c-*myc* or c-*erb*B-2/*neu* prooncogenes in human breast carcinomas: correlations with poor prognosis", *Oncogene Res.*, 3:21-31 (1988).
Hancock et al., "A monoclonal antibody against the c-*erb*B-2 protein enhances the cytoxicity of *cis*-diamminedichloroplatinum against human breast and ovarian tumor cell", *Cancer Res.*, 51:4575-4580 (1991).
Harwerth et al., "Monoclonal antibodies against the extracellular domain of the erbB-2 receptor function as partial ligand agonists", *J Biol. Chem.*, 267:15160-15167 (1992).
Holmes et al., "Identification of heregulin, a specific activator of p185$^{erbB2}$", *Science*, 256:1205-1210 (1992).
Hudziak et al., "p185*HER2* monoclonal antibody has antiproliferative effects in vitro and sensitizes human breast tumor cells to tumor necrosis factor", *Mol Cell Biol.* 9(3):1165-72 (1989).
Jones et al., "Replacing the complementarity-determining regions in a human antibody with those from a mouse", *Nature*, 321:522-525 (1986).
Kasprzyk et al., "Therapy of an animal model of human gastric cancer using a combination of anti-*erb*B-2 monoclonal antibodies", *Cancer Research*, 52:2771-2776 (1992).
Kelley et al., "Antigen binding thermodynamics and antiproliferative effects of chimeric and humanized anti-p185*HER2* antibody fab fragments", *Biochemistry*, 31(24):5434-411, (1992).
Kelley, R.F. & O'Connell, M.P., "Thermodynamic analysis of an antibody functional epitope", *Biochemistry*, 32(27):6828-35 (1993).
Kern et al., "p185*neu* expression in human lung adenocarcinomas predicts shortened survival", *Cancer Res.*, 50:5184-5191 (1990).
King et al., Amplification of a novel v-*erb*B-related gene in a human mammary carcinoma:, *Science*, 229:974-976 (1985).
Klapper et al. , "A subclass of tumor-inhibitory monoclonal antibodies to erbB-2/HER2 blocks crosstalk with growth factor receptors", *Oncogene*, 14:2099-2109 (1997).
Kotts et al., "Differential growth inhibition of human carcinoma cells exposed to monoclonal antibodies directed against the extracellular domain of the HER2/ERBB2 protooncongene", In Vitro, 26(3):59A (1990).
Kumar et al., "Regulation of phosphorylation of the c-*erb*B-2/HER2 gene product by a monoclonal antibody and serum growth factor(s) in human mammary carcinoma cells", *Mol. Cell. Biol.*, 11(2):979-986 (1991).
Lewis et al., "Differential responses of human tumor cell lines to anti-p185$^{HER2}$ monoclonal antibodies", *Cancer Immunol. Immunother.*, 37:255-263 (1993).
Lewis et al., "Growth regulation of human breast and ovarian tumor cells by heregulin: evidence for the requirement of erbB2 as a critical component in mediating heregulin responsiveness", *Cancer Research*, 56:1457-1465 (1996).
Lowman, H. B., "Phage display of peptide libraries on protein scaffolds", *Methods Mol Biol*, 87:249-64 (1998).
Maier et al., "Requirements for the internalization of a murine monoclonal antibody directed against the HER-2/*neu* gene product c-*erb*B-2", *Cancer Res.*, 51:5361-5369 (1991).
Marchionni et al., "Glial growth factors are alternatively spliced erbB2 ligands expressed in the nervous system", *Nature*, 362:312-318 (1993).
McCann et al., "c-*erb*B-2 oncoprotein expression in primary human tumors", *Cancer*, 65:88-92 (1990).
McKeage, K. & Perry, C. M., "Trastuzumab: a review of its use in the treatment of metastatic breast cancer overexpressing HER2", *Drugs*, 62(1):209-43 (2002).
McKenzie et al., "Generation and charactierization of monoclonal antibodies specific for the human *neu* oncogene product, p185", *Oncogene*, 4:543-548 (1989).
Myers et al., "Biological effects of monoclonal antireceptor antibodies reactive with *neu* oncogene product p185*neu*", *Meth. Enzym.*, 198:277-290 (1991).
Park et al., "Amplification, overexpression and rearrangement of the *erb*B-2 protooncogene in primary human stomach carcinomas", *Cancer Res.*, 49:6605-6609 (1989).
Pietras et al., "Antibody to HER-2/*neu* receptor blocks DNA repair after cisplatin in human breast and ovarian cancer cells", *Oncogene*, 9:1829-1838 (1994).
Presta, "Antibody engineering", *Curr. Op. Struct. Biol.*, 2:593-596 (1992).
Presta et al., Humanization of an antibody directed against IgE, *J Immunol.*, 151:2623-2632 (1993).
Riechmann et al., "Reshaping human antibodies for therapy", *Nature*, 332:323-329 (1988).
Ross et al., "Prognostic significance of HER-2/*neu* gene amplification status by fluorescence in situ hybridization of prostate carcinoma", *Cancer*, 79:2162-70 (1997).
Ross et al., "HER-2/neu gene amplification status in prostate cancer by fluorescence in situ hybridization", *Hum. Pathol.*, 28:827-33 (1997).
Sadasivan et al., "Overexpression of HER-2/neu may be an indicator of poor prognosis in prostate cancer", *J. Urol.* 150:126-31 (1993).
Sarup et al., "Characterization of an anti-p185$^{HER2}$ monoclonal antibody that stimulates receptor function and inhibits tumor cell growth", *Growth Regulation*, 1:72-82 (1991).
Schaefer et al., "Heregulin: a novel heregulin isoform that is an autocrine growth factor for the human breast cancer cell line, MDA-MB-175", *Oncogene*, 15:1385-1394 (1997).
Xu et al., "Antibody-induced growth inhibition is mediated through immunochemically and functionally distinct epitopes on the extracellular domain of the c-*erb*B-2 (HER-2/*neu*) gene", *Int. J. Cancer*, 53:401-408 (1993).
Yamamoto et al,. "Similarity of protein encoded by the human c-*erb*-B-2 gene to epidermal growth factor receptor", *Nature*, 319:230-234 (1986).
Yokota et al., "Amplification of c-*erb*B-2 oncogene in human adenocarcinomas in vivo", *Lancet*, 1:765-767 (1986).
Yonemura et al., "Evaluation of immunoreactivity for erbB-2 protein as a marker of poor short term prognosis in gastric cancer", *Cancer Res.*, 51:1034-1038 (1991).
Zhau et al.,"Amplification and expression of the c-erb B-2/neu protooncogene in human bladder cancer", *Mol. Carcinog.*, 3:354-357 (1990).
Gerstner, R. B. et al., "Sequence Plasticity in the Antigen-Binding Site of a Therapeutic Anti-HER 2 Antibody", Journal of Molecular Biology, London, GB, vol. 321 (Aug. 30, 2002), pp. 851-862 XP002972421 ISSN: 0022-2836.
Lowman, H. B. et al., "Phage Display of Peptide Libraries on Protein Scaffolds" Methods in Molecular Biology, Human Press Inc., Clifton, NJ, US, vol. 87 (1998) pp. 249-264 XP000985641.
Sidhu, S. S. et al., "Phage Display for Selection of Novel Binding Peptides", Methods in Enzymology, Academic Press Inc., san Deigo, CA, US, vol. 328, (2000) pp. 333-363 XP000984091 ISSN: 0076-6879.
Schier et al., "Isolation of picomolar affinity anti-c-erbB-2 single-chain Fv by molecular evaluation of the complementarity determining regions in the center of the antibody binding site", *J Mol Biol.*, 263(4):551-67 (1996).
Scott et al., "p185$^{HER2}$ signal transduction in breast cancer cells", *J Biol. Chem.*, 266:14300-5 (1991).
Semba et al., "A v-*erb*B-related protooncogene c-*erb*B-2 is distinct from the c-*erb*B-1/epidermal growth factor-receptor gene and is amplified in a human salivary gland adenocarcinoma", *PNAS (USA)*, 82:6497-6501 (1985).
Shawver et al., "Ligand-like effects induced by anti-c-erbB-2 antibodies do not correlate with and are not required for growth inhibition of human carcinoma cells", *Cancer Res.*, 54:1367-1373 (1994).
Shepard et al., "Monoclonal antibody therapy of human cancer: taking the HER2 protooncogene to the clinic", *J Clin. Immunol.*, 11(3):117-127 (1991).
Sidhu et al., "Phage display for selection of novel binding peptides", *Methods Enzymol*, 328: 333-63 (2000).

Slamon et al., "Human breast cancer: correlation of relapse and survival with amplification of the HER-2/*neu* oncogene", *Science*, 235:177-182 (1987).

Slamon et al., "Studies of the HER-2/*neu* proto-oncogene in human breast and ovarian cancer", *Science*, 244(4905):707-12 (1989).

Sliwkowski et al., "Coexpression of *erb*B2 and *erb*B3 proteins reconstitutes a high affinity receptor for heregulin", *J Biol. Chem.*, 269(20):14661-14665 (1994).

Stancovski et al., "Mechanistic aspects of the opposing effects of monoclonal antibodies to the ERBB2 receptor on tumor growth", *PNAS (USA)*, 88:8691-8695 (1991).

Tagliabue et al., "Selection of monoclonal antibodies which induce internalization and phosphorylation of p185$^{HER2}$ and growth inhibition of cells with HER2/*neu* gene amplification ", *Int. J. Cancer*, 47:933-937 (1991).

Vitetta et al., "Monoclonal antibodies as agonists: an expanded role for their use in cancer therapy", *Cancer Research*, 54:5301-5309 (1994).

Weiner et al., "Expression of the *neu* gene-encoded protein (P185*neu*) in human non-small cell carcinomas of the lung", *Cancer Res.*, 50:421-425 (1990).

Wen et al., "Structural and functional aspects of the multiplicity of neu differentiation factors", *Mol. Cell Biol.*, 14(3):1909-1919 (1994).

Williams et al , "Expression of c-erbB-2 inhuman pancreatic adenocarcinomas", *Pathobiology*, 59:46-52 (1991).

\* cited by examiner

| Library | chain | Amino acid |
|---|---|---|
| 1 | Light | 94 |
|   | Heavy | 33,50,56,58,95 |
| 2 | Light | 30,91,92 |
|   | Heavy | 50,95,99,100a |
| 3 | Light | 49,53,91 |
|   | Heavy | 98,99,100,100a |
| 4 | Light |  |
|   | Heavy | 96,97,98,99,100 |
| 5 | Light | 49,53,55 |
|   | Heavy | 100,102 |

Library 1   Library 2   Library 3   Library 4   Library 5

Figure 3

| residue | 4D5 | φ | LIB | D | E | K | R | H | G | S | T | C | N | Q | A | V | L | I | M | P | F | W | Y | Nu | Nt |
|---|---|---|---|---|---|---|---|---|---|---|---|---|---|---|---|---|---|---|---|---|---|---|---|---|---|
| Class 1 | | | | | | | | | | | | | | | | | | | | | | | | | |
| VL30 | N | N | 2 | | | | | | 3% | 53% | | | 34% | | | | | | | | | | | 31 | 78 |
| VH33 | Y | Y | 1 | | | | | | | | | | | | | | | | | | | | 39% | 61% | 31 | 68 |
| VH50 | R | R | 1 | | | | 100% | | | | | | | | | | | | | | | | | | 31 | 68 |
| VH56 | Y | Y | 2 | | | | 100% | | | | | | | | | | | | | | | 10% | 13% | 74% | 31 | 78 |
| VH58 | R | R | 1 | | | | | | | | | | | | | | 23% | 6% | 3% | | 26% | 59% | 15% | 31 | 68 |
| VH95 | W | W | 1 | | | 12% | 56% | | | | | | | | | | | | | | 6% | 82% | 12% | 31 | 68 |
| VH99 | G | W | 1 | | | | | | 100% | | | | | | | | | | | | | | | 30 | 67 |
| VH99 | G | G | 2 | | | | | | 90% | 3% | 3% | | | | 3% | | 1% | | | | | | | 32 | 78 |
| VH100a | Y | Y | 2 | | | | | | | | | | | | | | | | | | | | 100% | 33 | 78 |
| VH100a | Y | Y | 3 | | | | | 19% | | | 1% | | | | | | | | | | 10% | | 88% | 70 | 71 |
| | | | | | | | | | | | | | | | | | | | | | | | | 33 | 78 |
| | | | | | | | | | | | | | | | | | | | | | | | | 69 | 70 |
| Class 2 | | | | | | | | | | | | | | | | | | | | | | | | | |
| VL49 | Y | F | 3 | 4% | | 2% | 2% | | 1% | 3% | 3% | | | | 1% | 13% | 12% | 4% | 6% | | 28% | 17% | 9% | 69 | 70 |
| VL49 | Y | W | 5 | 4% | 16% | | | | | | | | 2% | | | 11% | 8% | 2% | 7% | | 7% | 31% | 9% | 57 | 57 |
| VL53 | F | F | 3 | | | | 1% | | | 1% | 2% | | | | | 2% | 5% | 2% | | | 67% | 16% | 2% | 69 | 70 |
| VL53 | F | W | 5 | | | | 1% | | | 2% | 1% | | | | | 2% | 2% | 3% | 2% | | 16% | 55% | 4% | 57 | 57 |
| VL55 | Y | W | 5 | 2% | | | | | 1% | 1% | 1% | | | | | 2% | 3% | 3% | 10% | | 12% | 58% | 12% | 57 | 57 |
| VL91 | H | F | 2 | | | | | 2% | | | | | | | | | 3% | 3% | | 4% | | 44% | 9% | 15% | 33 | 78 |
| VL91 | | W | 3 | | | | | 26% | | | | | | | | | | | | | | 45% | 1% | 32% | 69 | 70 |
| VL92 | Y | F | 2 | | | | | 19% | | | | | | | | | | | 1% | | | 16% | 41% | 16% | 31 | 78 |
| VL94 | T | T | 1 | | | | | | 3% | 3% | 45% | | 3% | | | | 2% | 14% | | 19% | | 5% | 27% | | 30 | 67 |
| VH100 | F | F | 3 | | | | | | | 5% | | | 5% | | | 2% | 14% | 7% | 26% | | 52% | 2% | 2% | 67 | 68 |
| VH100 | | W | 5 | | | | 1% | | | | | | | | | | | | 17% | 7% | 30% | 34% | 3% | 54 | 55 |
| Class 3 | | | | | | | | | | | | | | | | | | | | | | | | | |
| VH98 | D | W | 3 | 2% | 2% | 2% | 6% | 6% | 2% | 2% | 3% | | 2% | 2% | 4% | 6% | 4% | 9% | 2% | 5% | 6% | 23% | 9% | 69 | 70 |
| VH102 | Y | V | 5 | | 3% | 6% | 4% | | 4% | 1% | 3% | | 3% | 3% | 6% | 19% | 12% | 6% | 14% | | | 9% | 3% | 57 | 57 |

Figure 4

| mutant | $k_{on}$ ($10^5$ M$^{-1}$ s$^{-1}$) | $k_{off}$ ($10^{-4}$ s$^{-1}$) | $K_D$ (37°C) (nM) |
|---|---|---|---|
| wt | 10 ± 1.6 | 3.5 ± 0.1 | 0.35 ± 0.05 |
| N30(V$_L$)S | 10 ± 3.4 | 4.0 ± 0.1 | 0.39 ± 0.11 |
| H91(V$_L$)F | 9.7 ± 3.3 | 3.6 ± 0.2 | 0.37 ± 0.15 |
| N30(V$_L$)S + H91(V$_L$)F + Y92(V$_L$)W | 11 ± 4.4 | 3.5 ± 0.3 | 0.31 ± 0.16 |
| T94(V$_L$)S | 9.3 ± 3.5 | 5.5 ± 0.2 | 0.59 ± 0.25 |
| D98(V$_H$)W | 17 ± 4.5 | 1.9 ± 0.2 | 0.11 ± 0.04 |
| Y100a(V$_H$)F | 9.0 ± 3.6 | 13 ± 0.2 | 1.4 ± 0.56 |
| Y102(V$_H$)V | 12 ± 1.4 | 6.2 ± 1.6 | 0.51 ± 0.15 |
| N30(V$_L$)S + H91(V$_L$)F + Y92(V$_L$)W + T94(V$_L$)S + D98(V$_H$)W + Y100a(V$_H$)F + Y102(V$_H$)V | 22 ± 3.1 | 8.4 ± 1.6 | 0.38 ± 0.04 |

Figure 7
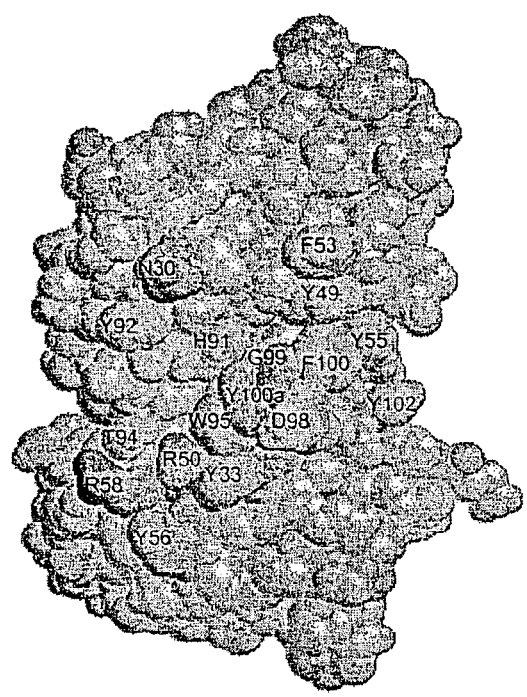 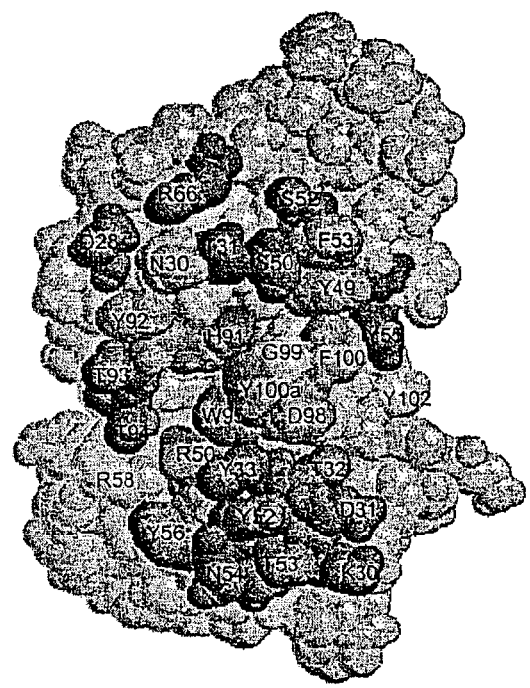

ANTI-HER2 ANTIBODY VARIANTS

This application claims the benefit under 35 U.S.C. 119(h) of provisional application Ser. No. 60/371,609, filed Apr. 10, 2002 which is herby incorporated by reference.

BACKGROUND OF THE INVENTION

1. Field of the Invention

The present invention concerns novel antibody variants, particularly anti-HER2 antibody variants.

2. Description of the Related Art

Members of the ErbB family of receptor tyrosine kinases are important mediators of cell growth, differentiation and survival. The receptor family includes four distinct members, including epidermal growth factor receptor (EGFR or ErbB1), HER2 (ErbB2 or $p185^{neu}$), HER3 (ErbB3) and HER4 (ErbB4 or tyro2).

$p185^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science* 244 (4905):707-12 (1989); and U.S. Pat. No. 4,968,603). To date, no point mutation analogous to that in the neu proto-oncogene has been reported for human tumors. Overexpression of ErbB2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet*, 1:765-767 (1986); Fukushige et al., *Mol Cell Biol.*, 6:955-958 (1986); Geurin et al., *Oncogene Res.*, 3:21-31 (1988); Cohen et al., *Oncogene*, 4:81-88 (1989); Yonemura et al., *Cancer Res.*, 51:1034 (1991); Borst et al., *Gynecol. Oncol.*, 38:364 (1990); Weiner et al., *Cancer Res.*, 50:421-425 (1990); Kern et al., *Cancer Res.*, 50:5184 (1990); Park et al., *Cancer Res.*, 49:6605 (1989); Zhau et al., *Mol. Carcinog.*, 3:354-357 (1990); Aasland et al. *Br. J. Cancer*, 57:358-363 (1988); Williams et al. *Pathobiology*, 59:46-52 (1991); and McCann et al., *Cancer*, 65:88-92 (1990). ErbB2 may be over-expressed in prostate cancer (Gu et al. *Cancer Lett.*, 99:185-9 (1996); Ross et al. *Hum. Pathol.*, 28:827-33 (1997); Ross et al. *Cancer*, 79:2162-70 (1997); and Sadasivan et al. *J. Urol.*, 150:126-31 (1993)).

Antibodies directed against the rat $p185^{neu}$ and human ErbB2 protein products have been described. Drebin and colleagues have raised antibodies against the rat neu gene product, $p185^{neu}$. See, for example, Drebin et al., *Cell*, 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of $p185^{neu}$ result in synergistic anti-tumor effects on neu-transformed NIH-3T3 cells implanted into nude mice. See also U.S. Pat. No. 5,824,311 issued Oct. 20, 1998.

Other anti-ErbB2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Hudziak et al., *Mol Cell Biol* 9(3):1165-72 (1989) describe the generation of a panel of anti-ErbB2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α. See also U.S. Pat. No. 5,677,171 issued Oct. 14, 1997. The anti-ErbB2 antibodies discussed in Hudziak et al., A., *Mol Cell Biol* 9(3):1165-72 (1989) are further characterized in Fendly et al., *Cancer Res* 50(5):1550-8 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

The murine monoclonal anti-HER2 antibody inhibits the growth of breast cancer cell lines that overexpress HER2 at the 2+ and 3+ level, but has no activity on cells that express lower levels of HER2 (Lewis et al., *Cancer Immunol. Immunother.* [1993]). Based on this observation, antibody 4D5 was humanized (Carter et al., *Proc. Natl. Acad. Sci. USA* 89: 4285-4289 [1992]). The humanized version designated HERCEPTIN® (huMAb4D5-8, rhuMAb HER2, U.S. Pat. No. 5,821,337) was tested in breast cancer patients whose tumors overexpress HER2 but who had progressed after conventional chemotherapy (Cobleigh et al., *J. Clin. Oncol.* 17: 2639-2648 [1999]). Most patients in this trial expressed HER2 at the 3+ level, though a fraction was 2+ tumors. Remarkably, HERCEPTIN® induced clinical responses in 15% of patients (complete responses in 4% of patients, and partial responses in 11%) and the median duration of those responses was 9.1 months. HERCEPTIN® received marketing approval from the Food and Drug Administration Sep. 25, 1998 for the treatment of patients with metastatic breast cancer whose tumors overexpress the ErbB2 protein.

SUMMARY OF THE INVENTION

The present invention is based on the finding that particular amino acids of the humanized anti-HER2 antibody hu4D5-8, determined by alanine scanning to be necessary for antigen binding, and other amino acids found by alanine scanning to be relatively unimportant for antigen binding, may be substituted to produce variants having high affinity for HER2. Preferred positions for possible mutations are shown in FIG. 2. Thus, while certain variants are discussed in detail herein, other variants with substitutions at one or more of the positions indicated in FIG. 2 are also contemplated and encompassed by the present invention.

In one aspect, the present invention relates to a polypeptide which comprises an antibody light chain variable domain comprising the hypervariable regions of SEQ ID NO: 1 wherein one or more amino acids selected from the group consisting of Q27($V_L$), D28($V_L$), N30($V_L$), T31($V_L$), A32($V_L$), Y49($V_L$), F53($V_L$), Y55($V_L$), R66($V_L$), H91($V_L$), Y92($V_L$), and T94($V_L$), numbered according to the Kabat numbering system, are substituted with any amino acid other than alanine.

In one embodiment, the invention relates to a polypeptide wherein the hypervariable regions of SEQ ID NO: 1 comprise amino acid substitutions at one or more positions selected from the group consisting of N30($V_L$), F53($V_L$), Y55($V_L$), H91($V_L$), Y92($V_L$), and T94($V_L$), and F100($V_L$).

In another embodiment, the invention concerns a polypeptide wherein the hypervariable regions of SEQ ID NO: 1 comprise amino acid substitutions at one or more positions selected from the group consisting of N30($V_L$), F53($V_L$), Y55($V_L$), H91($V_L$), Y92($V_L$), and T94($V_L$).

In yet another embodiment, the invention concerns a polypeptide wherein the hypervariable regions of SEQ ID NO: 1 comprise one or more amino acid substitutions selected from the group consisting of D28($V_L$)Q; D28($V_L$)G; N30($V_L$)S; T31($V_L$)S; A32($V_L$)G; Y49($V_L$)W, Y49($V_L$)D, Y49($V_L$)V; F53($V_L$)W. F53($V_L$)V, F53($V_L$)Q, Y55($V_L$)W, R66($V_L$)N, H91($V_L$)F, H91($V_L$)Y, Y92($V_L$)W, and T94($V_L$)S.

In a further embodiment, the hypervariable regions of SEQ ID NO: 1 comprise one or more amino acid substitutions selected from the group consisting of D28($V_L$)Q; D28($V_L$)G; N30($V_L$)S; T31($V_L$)S; A32($V_L$)G; Y49($V_L$)W, Y49)D, Y49($V_L$)V; F53($V_L$)W, F53($V_L$)V, F53($V_L$)Q, Y55($V_L$)W, R66($V_L$)N, H91($V_L$)F, H91($V_L$)Y, and Y92($V_L$)W In a still further embodiment, the hypervariable regions of SEQ ID NO: 1 comprise one or more amino acid substitutions selected from the group consisting of Y49($V_L$)D, F53($V_L$)W, and Y55($V_L$)W. In specific embodiments, the polypeptide can contain two or three of the indicated amino acid substitutions.

In a further embodiment, the invention concerns a polypeptide, wherein the hypervariable regions of SEQ ID NO: 1 comprise one or more amino acid substitutions selected from the group consisting of N30($V_L$)S, F53($V_L$)W, Y55($V_L$)W, H91($V_L$)F, Y92($V_L$)W and T94($V_L$)S. In a specific embodiment, N30($V_L$) is substituted with S, H91($V_L$) is substituted with F, and Y92($V_L$) is substituted with W.

In all embodiments, the polypeptide can, for example, be an antibody, such as a humanized (including chimeric) or human antibody, including antibody fragments, such as, for example, Fv, Fab, Fab' and F(ab')$_2$ fragments.

In another aspect, the invention concerns a polypeptide which comprises an antibody heavy chain variable domain comprising the hypervariable regions of SEQ ID NO: 2 wherein one or more amino acids selected from the group consisting of W95($V_H$), D98($V_H$), F100($V_H$), Y100a($V_H$), and Y102($V_H$), numbered according to the Kabat numbering system, are substituted with any amino acid other than alanine.

In one embodiment, in the foregoing polypeptide, the hypervariable regions of SEQ ID NO: 2 comprise one or more amino acid substitutions selected from the group consisting of W95($V_H$)Y, D98($V_H$)W, D98($V_H$)R, D98($V_H$)K, D98($V_H$)H, F100($V_H$)P, Y100a($V_H$)F, Y102($V_H$)V, Y102($V_H$)K, and Y102($V_H$)L.

In another embodiment, the hypervariable regions of SEQ ID NO: 2 comprise one or more amino acid substitutions selected from the group consisting of, D98($V_H$)W, Y100a($V_H$)F, and Y102($V_H$)V.

In yet another embodiment, the hypervariable regions of SEQ ID NO: 2 comprise one or more amino acid substitutions selected from the group consisting of F100($V_H$)P and Y102($V_H$)K.

In a specific embodiment, the polypeptide comprises the amino acid substitutions F100($V_H$)P and Y102($V_H$)K.

Just as before, the polypeptide can, for example be an antibody, such as a humanized (including chimeric), or human antibody, including antibody fragments, such as, e.g. Fv, Fab, Fab' and F(ab')$_2$ fragments.

In a further aspect, the invention concerns an antibody that is capable of binding to the extracellular domain of HER2, which comprises the hypervariable regions of SEQ ID NO: 1 wherein one or more amino acids selected from the group consisting of Q27($V_L$), D28($V_L$), N30($V_L$), T31($V_L$), A32($V_L$), Y49($V_L$), F53($V_L$), Y55($V_L$), R66($V_L$), H91($V_L$), Y92($V_L$), and T94($V_L$), numbered according to the Kabat numbering system, are substituted with any amino acid other than alanine.

In one embodiment, in the antibody one or more amino acids selected from the group consisting of N30($V_L$), F53($V_L$), Y55($V_L$), H91($V_L$), Y92($V_L$), and T94($V_L$), numbered according to the Kabat numbering system, are substituted with any amino acid other than alanine.

In another embodiment, one or more amino acids selected from the group consisting of N30($V_L$), F53($V_L$), Y55($V_L$), H91($V_L$), Y92($V_L$), and T94($V_L$), numbered according to the Kabat numbering system, are substituted with any amino acid other than alanine.

In yet another embodiment, the hypervariable regions of SEQ ID NO: 1 comprise one or more amino acid substitutions selected from the group consisting of D28($V_L$)Q; D28($V_L$)G; N30($V_L$)S; T31($V_L$)S; A32($V_L$)G; Y49($V_L$)W, Y49($V_L$)D, Y49($V_L$)V; F53($V_L$)W. F53($V_L$)V, F53($V_L$)Q, Y55($V_L$)W, R66($V_L$)N, H91($V_L$)F, H91($V_L$)Y, Y92($V_L$)W, and T94($V_L$)S.

In a further embodiment, the hypervariable regions of SEQ ID NO: 1 comprise one or more amino acid substitutions selected from the group consisting of D28($V_L$)Q; D28($V_L$)G; N30($V_L$)S; T31($V_L$)S; A32($V_L$)G; Y49($V_L$)W, Y49($V_L$)D, Y49($V_L$)V; F53($V_L$)W, F53($V_L$)V, F53($V_L$)Q, Y55($V_L$)W, R66($V_L$)N, H91($V_L$)F, H91($V_L$)Y, and Y92($V_L$)W.

In a still further embodiment, the hypervariable regions of SEQ ID NO: 1 comprise one or more amino acid substitutions selected from the group consisting of Y49($V_L$)D, F53($V_L$)W, and Y55($V_L$)W. In specific embodiments, the antibody may contain two or three, e.g. all three, of the indicated substitutions.

The invention specifically includes antibodies in which the hypervariable regions of SEQ ID NO: 1 comprise one or more amino acid substitutions selected from the group consisting of N30($V_L$)S, F53($V_L$)W, Y55($V_L$)W, H91($V_L$)F, Y92($V_L$)W, T94($V_L$)S. Thus, in a particular embodiment, the invention concerns an antibody wherein N30($V_L$) is substituted with S, H91($V_L$) is substituted with F, and Y92($V_L$) is substituted with W.

The antibodies include humanized (including chimeric) and human antibodies, including antibody fragments, e.g. Fv, Fab, Fab' and F(ab')$_2$ fragments.

In a further aspect, the invention concerns an antibody that is capable of binding to the extracellular domain of HER2, which comprises an antibody heavy chain variable domain comprising the hypervariable regions of SEQ ID NO: 2 wherein one or more amino acids selected from the group consisting of W95($V_H$), D98($V_H$), F100($V_H$), Y100a($V_H$), and Y102($V_H$), numbered according to the Kabat numbering system, are substituted with any amino acid other than alanine.

In one embodiment, the invention concerns an antibody wherein the hypervariable regions of SEQ ID NO: 2 comprise one or more amino acid substitutions selected from the group consisting of W95($V_H$)Y, D98($V_H$)W, D98($V_H$)R, D98($V_H$)K, D98($V_H$)H, F100($V_H$)P, F100($V_H$)L, F100($V_H$)M, Y100a($V_H$)F, Y102($V_H$)V, Y102($V_H$)K, and Y102($V_H$)L.

In another embodiment, in the antibody of the present invention the hypervariable regions of SEQ ID NO: 2 comprise one or more amino acid substitutions selected from the group consisting of, D98($V_H$)W, Y100a($V_H$)F, and Y102($V_H$)V.

In yet another embodiment, the hypervariable regions of SEQ ID NO: 2 comprise one or more amino acid substitutions selected from the group consisting of F100($V_H$)P and Y102($V_H$)K or Y102($V_H$)L. The antibody may, for example, comprise the amino acid substitutions F100($V_H$)P and Y102($V_H$)K, or F100($V_H$)P and Y102($V_H$)L.

Just as in other aspects of the invention, the antibody can be humanized (including chimeric), or human, including antibody fragments, such as, for example, Fv, Fab, Fab' and F(ab')$_2$ fragments.

In a further aspect, the invention concerns an antibody that is capable of binding to the extracellular domain of HER2, which comprises the hypervariable regions of SEQ ID NOs: 1 and 2 wherein one or more amino acids selected from the group consisting of Q27($V_L$), D28($V_L$), N30($V_L$), T31($V_L$), A32($V_L$), Y49($V_L$), F53($V_L$), Y55($V_L$), R66($V_L$), H91($V_L$), Y92($V_L$), T94($V_L$), W95($V_H$), D98($V_H$), F100($V_H$), Y100a($V_H$), and Y102($V_H$), numbered according to the Kabat numbering system, are substituted with any amino acid other than alanine.

In one embodiment, in the antibody the hypervariable regions of SEQ ID NOs: 1 and 2 comprise one or more amino acid substitutions selected from the group consisting of N30($V_L$)S, F53($V_L$)W, Y55($V_L$)W, H91($V_L$)F, Y92($V_L$)W, T94($V_L$)S, D98($V_H$)W, Y100a($V_H$)F, and Y102($V_H$)V.

In another embodiment, N30($V_L$) is substituted with S, H91($V_L$) is substituted with F, Y92($V_L$) is substituted with W, T94($V_L$) is substituted with S, D98($V_H$) is substituted with W, Y100a($V_H$) is substituted with F, and Y102($V_H$) is substituted with V.

In a specific embodiment, D98($V_H$) is substituted with W.

In yet another embodiment, the hypervariable regions of SEQ ID NOs 1 and 2 comprise one or more amino acid substitutions selected from the group consisting of D28($V_L$)Q; D28($V_L$)G; N30($V_L$)S; T31($V_L$)S; A32($V_L$)G; Y49($V_L$)W, Y49($V_L$)D, Y49($V_L$)V; F53($V_L$)W, F53($V_L$)V, F53($V_L$)Q, Y55($V_L$)W, R66($V_L$)N, H91($V_L$)F, H91($V_L$)Y, Y92($V_L$)W, T94($V_L$)S, F100($V_L$)W; W95($V_H$)Y, D98($V_H$)W, D98($V_H$)R, D98($V_H$)K, D98($V_H$)H, F100($V_H$)P, F100($V_H$)L, F100($V_H$)M, Y100a($V_H$)F, Y102($V_H$)V, Y102($V_H$)K, and Y102($V_H$)L.

In a further embodiment, the hypervariable regions of SEQ ID NOs 1 and 2 comprise one or more amino acid substitutions selected from the group consisting of Y49($V_L$)D, F53($V_L$)W, Y55($V_L$)W, D98($V_H$)W, F100($V_H$)P, and Y102($V_H$)L.

In a still further embodiment, the hypervariable regions of SEQ ID NOs: 1 and 2 comprise the following substitutions: Y49($V_L$)D, F53($V_L$)W, Y55($V_L$)W, F100($V_H$)P, and Y102($V_H$)L. In a particular embodiment, the hypervariable regions of SEQ ID NO 2 may further comprise the substitution D98($V_H$)W.

In an additional embodiment, the binding affinity of the antibody for the HER2 extracellular domain is at least about three-fold better than the binding affinity of humanized monoclonal antibody 4D5-8 for the HER2 extracellular domain.

Again, the antibody can, for example, be humanized (including chimeric), or human, including antibody fragments, such as Fv, Fab, Fab' and F(ab')$_2$ fragments.

In a different aspect, the invention concerns an antibody that is capable of binding to the extracellular domain of HER2 wich comprises the light chain variable domain of SEQ ID NO: 1 wherein one or more amino acids selected from the group consisting of Q27($V_L$), N30($V_L$), Y49($V_L$), F53($V_L$), Y55($V_L$), H91($V_L$), Y92($V_L$), and T94($V_L$), numbered according to the Kabat numbering system, are substituted with any amino acid other than alanine.

In a particular embodiment, the light chain variable domain of SEQ ID NO: 1 comprises one or more amino acid substitutions selected from the group consisting of N30($V_L$) S, Y49($V_L$)F, Y49($V_L$)W, F53($V_L$)W, Y55($V_L$)W, H91($V_L$)F, Y92($V_L$)W, and T94($V_L$)S.

In another embodiment, N30($V_L$) is substituted with S, H91($V_L$) is substituted and Y92($V_L$) is substituted with W.

In a still further aspect, the invention concerns a humanized anti-HER2 antibody 4D5-8, comprising one or more amino acid substitutions selected from the group consisting of N30($V_L$)S, Y49($V_L$)F, Y49($V_L$)W, F53($V_L$)W, Y55($V_L$)W, H91($V_L$)F, Y92($V_L$)W, T94($V_L$)S, D98($V_H$)W, F100($V_H$)P, Y100a($V_H$)F, and Y102($V_H$)V, numbered according to the Kabat numbering system.

In one embodiment, the humanized anti-HER2 antibody 4D5-8 comprises one or more amino acid substitutions selected from the group consisting of Y49($V_L$)D, F53($V_L$)W, Y55($V_L$)W, F100($V_H$)P, Y102($V_H$)K, and Y102($V_H$)L.

In another embodiment, the humanized anti-HER2 antibody 4D5-8 further comprises the amino acid substitution D98($V_H$)W.

In yet another embodiment, the humanized anti-HER2 antibody 4D5-8 comprises one or more of the amino acid substitutions selected from the group consisting of Y49($V_L$)D, F53($V_L$)W, and Y55($V_L$)W.

In a further embodiment, the humanized anti-HER2 antibody 4D5-8 comprises one or more of the amino acid substitutions selected from the group consisting of F100($V_H$)P, Y102($V_H$)K, and Y102($V_H$)L.

In a still further embodiment, the humanized anti-HER2 antibody 4D5-8 comprises the following amino acid substitutions: Y49($V_L$)D, F53($V_L$)W, Y55($V_L$)W, F100($V_H$)P, and Y102($V_H$)K.

In a different embodiment, the humanized anti-HER2 antibody 4D5-8 comprises the following amino acid substitutions: Y49($V_L$)D, F53($V_L$)W, Y55($V_L$)W, F100($V_H$)P, and Y102($V_H$)L.

In another aspect, the invention concerns an article of manufacture comprising a container, a composition contained therein, and a package insert or label indicating that the composition can be used to treat cancer characterized by the overexpression of HER2, wherein the composition comprises the antibody of original claim 60 or 61. The cancer may, for example, be breast cancer.

In yet another aspect, the invention concerns an antibody variant of a parent antibody which binds HER2, comprising an amino acid substitution at position 98 of a heavy chain variable domain thereof, and wherein the binding affinity of the antibody variant for HER2 is better than the binding affinity of the parent antibody for HER2. In a specific embodiment, the amino acid at position 98 is substituted with W. The parent antibody may be, without limitation, a humanized antibody.

In a different aspect, the invention concerns a method for isolating high-affinity variants of a humanized anti-HER2 antibody, comprising:

(a) producing anti-HER2 variants with substitutions at one or more amino acids selected from the group consisting Q27 ($V_L$), D28($V_L$), N30($V_L$), T31($V_L$), A32($V_L$), Y49($V_L$), F53 ($V_L$), Y55($V_L$), R66($V_L$), H91($V_L$), Y92($V_L$), T94($V_L$), W95 ($V_H$), D98($V_H$), F100($V_H$), Y100a($V_H$), and Y102($V_H$), within the hypervariable regions of SEQ ID NOs: 1 and 2, wherein numbering is according to the Kabat numbering system;

(b) measuring binding affinities of the variants produced in (a) for HER2 extracellular domain; and (c) selecting for high-affinity variants.

BRIEF DESCRIPTION OF THE DRAWINGS

In FIGS. 1A and 1B the hypervariable region residues are identified by underlining. As discussed in more detail below, the hypervariable regions were determined according to both a standard sequence definition (Kabat, E. A. et al., *Sequences of Proteins of Immunological Interest* (National Institutes of Health, Bethesda, Md., 1987)) and a structural definition (Chothia, C. & Lesk, A. M., *J Mol Biol* 196(4),: 901-17 (1987)). In FIG. 1A, these regions are designated as $V_L$-hypervariable region 1 (comprising the amino acid sequence RASQDVNTAVA (SEQ ID NO: 19)), $V_L$-hypervariable region 2 (comprising the amino acid sequence SASFLYS (SEQ ID NO: 20)), and $V_L$-hypervariable region 3 (comprising the amino acid sequence QQHYTTPPT (SEQ ID NO: 21)). In FIG. 1B, the hypervariable regions are designated as $V_H$-hypervariable region 1 (comprising the amino acid sequence GFNIKDTYIH (SEQ ID NO: 22)), $V_H$-hypervariable region 2 (comprising the amino acid sequence RIYPTNGYTRYADSVKG (SEQ ID NO: 23)), and $V_H$-hypervariable region 3 (comprising the amino acid sequence WGGDGFYAMDY (SEQ ID NO: 24)).

FIG. 3 shows amino acid substitutions in Fab-phage clones. For each position, the source library, wild-type residue, and the most commonly observed residue (φ) after 4 rounds of selection are shown. The observed frequency (%) of each amino acid at each position (Kabat numbering; Johnson, G. & Wu, T. T., *Nucleic Acids Res* 29(1):205-6 (2001)) was calculated based upon the number of unique sequenced clones ($N_U$; that is, removing sibling clones) and normalized for degenerate codons, codon bias and the total number of unique sequences (siblings removed). The wild-type and most-common frequencies are shown in bold and underlining, respectively. $N_T$, total number of sequenced clones (including siblings) for this position.

FIG. 4 shows antigen-binding kinetics of Fab mutants at 37° C. Values for $k_{on}$ and $k_{off}$ were measured by surface plasmon resonance (SPR) on a BIAcore 2000 or BIAcore 3000. These represent a mean of 4 measurements at four different densities of HER2-ECD ranging from 86 to 380 RU's. § indicates data for one mutant, Y92($V_L$)W, which showed poor expression and HER2 binding, suggesting that this mutant was misfolded. Multiple mutants are M.3 (N30 ($V_L$)S+H91($V_L$)F+Y92($V_L$)W) and M.7 (N30($V_L$)S+H91 ($V_L$)F+Y92($V_L$)W+T94($V_L$)S+D98($V_H$)W+Y100a($V_H$)F+ Y102($V_H$)V).

FIG. 7 illustrates a comparison of sequence variability (A) and Ala-scan results (B) on the hu4D5-8 structure. Residues selected from phage libraries (A) fall into 3 categories: Class 1, low variability (residues N30', G99', Y100a, W95, R50', Y33, R58', and Y56), Class 2, moderate variability (residues Y92, H91', T94', F53', Y49, Y55, and F100') and Class 3, high variability (residues Y102 and D98'). (B) Alanine scan results (Kelley, R. F. & O'Connell, M. P., *Biochemistry* 32(27):6828-35 (1993)) showing residues with effects on $K_D$ of 50-fold to 5000-fold (residues H91', Y100 a, W95, and R50'), 1.5 to 2 fold (residues Y92, N30', F53', Y49, F100', and D98'), and <1.5-fold (including small improvements in $K_D$) (residues D28', R66', T31', S50', S52', Y55, T93', T94', Y33, T32', Y56, Y52, D31', N54', T53', and K30').

DETAILED DESCRIPTION OF THE PREFERRED EMBODIMENT

Figure 1A:
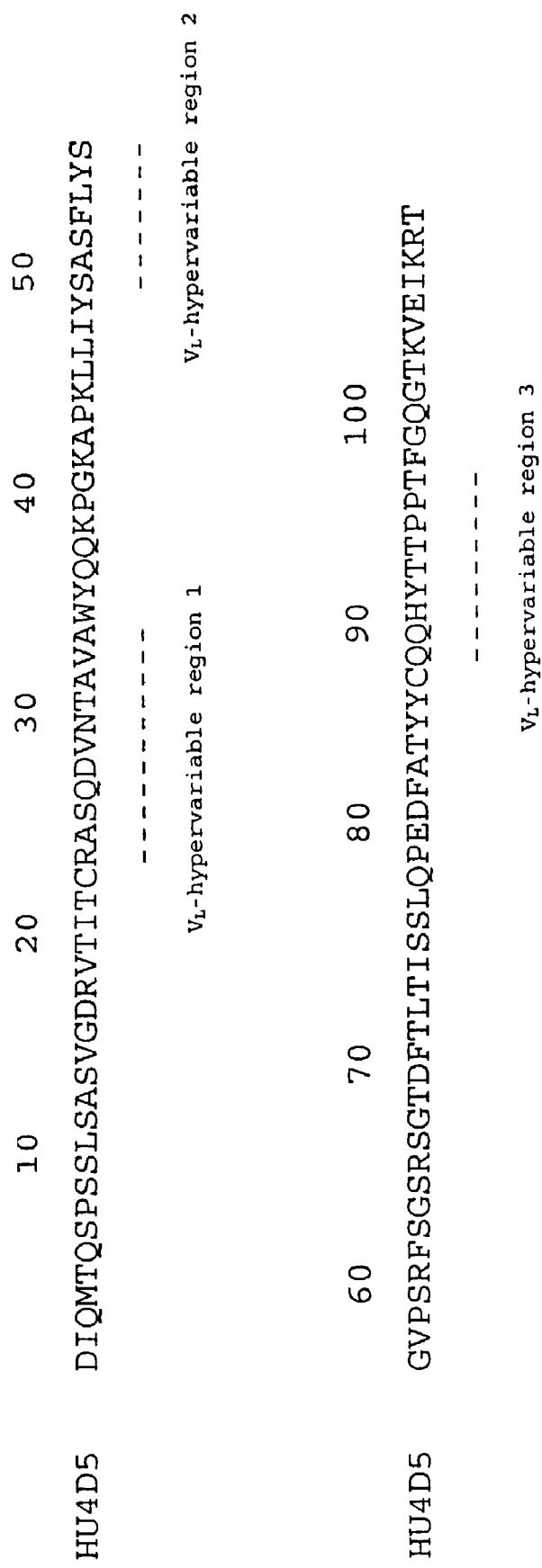
FIG. 1A shows the light chain variable domain ($V_L$) amino acid residues of huMAb4D5-8 (SEQ ID NO. 1).

The present invention is based on the identification of variants of a humanized anti-HER2 antibody, hu4D5-8, having HER2 binding affinity equal to or greater than the parent antibody. These variants were identified from a set of Fab libraries in which nineteen positions in the light and/or heavy variable domains were substituted with all 20 amino acids. The positions were selected for substitutions based in part on alanine scanning mutagenesis of the hu4D5-8 variable regions. Sequence variability within the high-affinity HER2-binding site of the hu4D5-8 antibody was tested by constructing monovalently displayed Fab-phage libraries, selecting for HER2 binding clones, and sequencing a large sample (50-70 clones) from each library pool at a point in the selection process where a high level of overall diversity (minimal siblings, that is occurrence of identical clones) was observed.

The binding affinities of soluble Fab fragments were also tested. A single mutant, D98($V_H$)W was found to have a 3-fold improvement in binding affinity over wild-type hu4D5-8 Fab.

Accordingly, the present invention concerns antibody variants, particularly anti-HER2 antibody variants.

1. Definitions

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994). One skilled in the art will recognize many methods and materials similar or equivalent to those described herein, which could be used in the practice of the present invention. Indeed, the present invention is in no way limited to the methods and materials described. For purposes of the present invention, the following terms are defined below.

Throughout the disclosure, the terms "ErbB2", "ErbB2 receptor", "c-Erb-B2", and "HER2" are used interchangeably, and, unless otherwise indicated, refer to a native sequence ErbB2 human polypeptide, or a functional derivative thereof. "her2", "erbB2" and "c-erb-B2" refer to the corresponding human gene. The terms "native sequence" or "native" in this context refer to a polypeptide having the sequence of a naturally occurring polypeptide, regardless its mode of preparation. Such native sequence polypeptides can be isolated from nature or can be produced by recombinant or synthetic means, or by any combination of these or similar methods.

Accordingly, "native" or "native sequence" HER2 polypeptides may be isolated from nature, produced by techniques of recombinant DNA technology, chemically synthesized, or produced by any combinations of these or similar methods. The amino acid sequence and encoding nucleotide sequence of a native human HER2 polypeptide is disclosed, for example, in Semba et al., *PNAS (USA)* 82:6497-65)2 (1985) and Yamamoto et al., *Nature* 319:230-234 (1986) (GenBank accession number Xo3363). ErbB2 comprises four domains (Domains 1-4). HER2 polypeptides from other non-human animals, e.g. mammalian species are also well known in the art. "Functional derivatives" include amino acid sequence variants, and covalent derivatives of the native polypeptides as long as they retain a qualitative biological activity of the corresponding native polypeptide. Amino acid sequence "variants" generally differ from a native sequence in the substitution, deletion and/or insertion of one or more amino acids anywhere within a native amino acid sequence. Deletional variants include fragments of the native polypeptides, and variants having N- and/or C-terminal truncations.

"Heregulin" (HRG) when used herein refers to a polypeptide which activates the ErbB2-ErbB3 and ErbB2-ErbB4 protein complexes (i.e. induces phosphorylation of tyrosine residues in the complex upon binding thereto). Various heregulin polypeptides encompassed by this term are disclosed in Holmes et al., *Science* 256:1205-1210 (1992); WO 92/20798; Wen et al., *Mol. Cell. Biol.* 14(3):1909-1919 (1994) and Marchionni et al., Nature 362:312-318 (1993), for example. The term includes biologically active fragments and/or variants of a naturally occurring HRG polypeptide, such as an EGF-like domain fragment thereof (e.g. $HRG\beta_{177-244}$).

The term "nucleic acid" refers to polynucleotides such as deoxyribonucleic acid (DNA), and, where appropriate, ribonucleic acid (RNA). The term also includes, as equivalents, analogs of either DNA or RNA made from nucleotide analogs, and as applicable, single (sense or antisense) and double-stranded polynucleotides. An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

As used herein, the term "vector" refers to a nucleic acid molecule capable of transporting another nucleic acid to which it has been linked. The term "expression vector" includes plasmids, cosmids or phages capable of synthesizing the subject HER2 protein encoded by the respective recombinant gene carried by the vector. Preferred vectors are those capable of autonomous replication and/expression of nucleic acids to which they are linked. In the present specification, "plasmid" and "vector" are used interchangeably, as the plasmid is the most commonly used form of vector.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of HER2.

The term "non-human mammal" refers to all members of the class Mammalia except humans. "Mammal" refers to any animal classified as a mammal, including humans, domestic and farm animals, and zoo, sports, or pet animals, such as mouse, rat, rabbit, pig, sheep, goat, cattle and higher primates.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. The term "progeny" refers to any and all offspring of every generation subsequent to an originally transformed cell or cell line. Mutant progeny that have the same function or biological activity as screened for in the originally transformed cell are included. Where distinct designations are intended, it will be clear from the context.

The term "antibody" herein is used in the broadest sense and specifically covers intact antibodies, monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

Antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include primatized antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains (Fab, Fab', F(ab')$_2$, Fabc, Fv), in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN7) as described in Table 3 of U.S. Pat. No. 5,821,337 expressly incorporated herein by reference; humanized 520C9 (WO93/21319) and humanized 2C4 antibodies as described in copending application Ser. No. 09/811115, incorporated herein by reference. Throughout the disclosure, the terms "huMAb4D5-8" and "hu4D5-8" are used interchangeably.

The term "hypervariable region" when used herein refers to the regions of an antibody variable domain which are hypervariable in sequence and/or form structurally defined loops. The hypervariable region comprises amino acid residues from a "complementarity determining region" or "CDR" (i.e. residues 24-34, 50-56, and 89-97 in the light chain variable domain and 31-35, 50-65, and 95-102 in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. residues 26-32, 50-52, and 91-96 in the light chain variable domain and 26-32, 53-55, and 96-101 in the heavy chain variable domain; Chothia and Lesk *J. Mol. Biol.* 196:901-917 (1987)). In both cases, the variable domain residues are numbered according to Kabat et al., supra, as discussed in more detail below. "Framework" or "FR" residues are those variable domain residues other than the residues in the hypervariable regions as herein defined.

A "parent antibody" or "wild-type" antibody is an antibody comprising an amino acid sequence which lacks one or more amino acid sequence alterations compared to an antibody variant as herein disclosed. Thus, the parent antibody generally has at least one hypervariable region which differs in amino acid sequence from the amino acid sequence of the corresponding hypervariable region of an antibody variant as herein disclosed. The parent polypeptide may comprise a native sequence (i.e. a naturally occurring) antibody (including a naturally occurring allelic variant), or an antibody with pre-existing amino acid sequence modifications (such as insertions, deletions and/or other alterations) of a naturally occurring sequence. Preferably the parent antibody is a chimeric, humanized or human antibody. For example, for purposes of the examples disclosed below, the wild-type antibody hu4D5-8 is huMAb4D5-8, as described in U.S. Pat. No. 5,821,337, without any amino acid substitutions or other modifications. Throughout the disclosure, "wild type," "WT," "wt," and "parent" or "parental" antibody are used interchangeably.

As used herein, "antibody variant" or "variant antibody" refers to an antibody which has an amino acid sequence which differs from the amino acid sequence of a parent antibody. Preferably, the antibody variant comprises a heavy chain variable domain or a light chain variable domain having an amino acid sequence which is not found in nature. Such variants necessarily have less than 100% sequence identity or similarity with the parent antibody. In a preferred embodiment, the antibody variant will have an amino acid sequence from about 75% to less than 100% amino acid sequence identity or similarity with the amino acid sequence of either the heavy or light chain variable domain of the parent antibody, more preferably from about 80% to less than 100%, more preferably from about 85% to less than 100%, more preferably from about 90% to less than 100%, and most preferably from about 95% to less than 100%. Identity or similarity with respect to this sequence is defined herein as the percentage of amino acid residues in the candidate sequence that are identical (i.e same residue) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity. The antibody variant is generally one which comprises one or more amino acid alterations in or adjacent to one or more hypervariable regions thereof.

An "amino acid alteration" refers to a change in the amino acid sequence of a predetermined amino acid sequence. Exemplary alterations include insertions, substitutions and deletions. An "amino acid substitution" refers to the replacement of an existing amino acid residue in a predetermined amino acid sequence; with another different amino acid residue.

A "replacement" amino acid residue refers to an amino acid residue that replaces or substitutes another amino acid residue in an amino acid sequence. The replacement residue may be a naturally occurring or non-naturally occurring amino acid residue.

An "amino acid insertion" refers to the introduction of one or more amino acid residues into a predetermined amino acid sequence. The amino acid insertion may comprise a "peptide insertion" in which case a peptide comprising two or more amino acid residues joined by peptide bond(s) is introduced into the predetermined amino acid sequence. Where the amino acid insertion involves insertion of a peptide, the inserted peptide may be generated by random mutagenesis such that it has an amino acid sequence which does not exist in nature. An amino acid alteration "adjacent a hypervariable region" refers to the introduction or substitution of one or more amino acid residues at the N-terminal and/or C-terminal end of a hypervariable region, such that at least one of the inserted or replacement amino acid residue(s) form a peptide bond with the N-terminal or C-terminal amino acid residue of the hypervariable region in question.

A "naturally occurring amino acid residue" is one encoded by the genetic code, generally selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val).

A "non-naturally occurring amino acid residue" herein is an amino acid residue other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA.

Throughout this disclosure, reference is made to the numbering system from Kabat, E. A., et al., *Sequences of Proteins of Immunological Interest* (National Institutes of Health, Bethesda, Md. (1987) and (1991). In these compendiums, Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. The Kabat numbering scheme is followed in this description. For purposes of this invention, to assign residue numbers to a candidate antibody amino acid sequence which is not included in the Kabat compendium, one follows the following steps. Generally, the candidate sequence is aligned with any immunoglobulin sequence or any consensus sequence in Kabat. Alignment may be done by hand, or by computer using commonly accepted computer programs; an example of such a program is the Align 2 program. Alignment may be facilitated by using some amino acid residues which are common to most Fab sequences. For example, the light and heavy chains each typically have two cysteines which have the same residue numbers; in $V_L$ domain the two cysteines are typically at residue numbers 23 and 88, and in the $V_H$ domain the two cysteine residues are typically numbered 22 and 92. Framework residues generally, but not always, have approximately the same number of residues, however the CDRs will vary in size. For example, in the case of a CDR from a candidate sequence which is longer than the CDR in the sequence in Kabat to which it is aligned, typically suffixes are added to the residue number to indicate the insertion of additional residues (see, e.g. residues 100abc in FIG. 1B). For candidate sequences which, for example, align with a Kabat sequence for residues 34 and 36 but have no residue between them to align with residue 35, the number 35 is simply not assigned to a residue.

As described herein, particular amino acid residues may be substituted with other residues. The designation for a substitution variant herein consists of a letter followed by a number followed by a letter. The first (leftmost) letter designates the amino acid in the wild-type antibody. The number refers to the amino acid position where the amino acid substitution is being made, and the second (right-hand) letter designates the amino acid that is used to replace the wild-type amino acid at that position. In addition, a referece to the antibody light chain variable domain ($V_L$) or heavy chain variable domain ($V_H$) may be inserted following the number to indicate the specific location of the residue and/or substitution. For example, the hu4D5-8 variants listed in FIG. 4 are designated with reference to the wild-type hu4D5-8 antibody light chain and heavy chain variable region amino acid sequences (SEQ ID NOs: 1 and 2).

As used herein, an antibody with a "high-affinity" is an antibody having a $K_D$, or dissociation constant, in the nanomolar (nM) range or better. A $K_D$ in the "nanomolar range or better" may be denoted by X nM, where X is a number less than about 10.

A molecule which "induces cell death" is one which causes a viable cell to become nonviable. The cell is generally one that expresses the ErbB2 receptor, especially where the cell overexpresses the ErbB2 receptor. Preferably, the cell is a cancer cell, e.g. a breast, ovarian, stomach, endometrial, salivary gland, lung, kidney, colon, thyroid, pancreatic, prostate or bladder cancer cell. In vitro, the cell may be a SK-BR-3, BT474, Calu 3, MDA-MB-453, MDA-MB-361 or SKOV3 cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e. in the absence of complement) and in the absence of immune effector cells. To determine whether the molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies are those which induce PI uptake in the PI uptake assay in BT474 cells (see below).

A molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one that overexpresses the ErbB2 receptor. Preferably the cell is a tumor cell, e.g. a breast, ovarian, stomach, endometrial, salivary gland, lung, kidney, colon, thyroid, pancreatic, prostate or bladder cancer cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the molecule which induces apoptosis is one which results in about 2 to 50 fold, preferably about 5 to 50 fold, and most preferably about 10 to 50 fold, induction of annexin binding relative to untreated cells, in an annexin binding assay using BT474 cells. Sometimes the pro-apoptotic molecule will be one which further blocks ErbB ligand activation of an ErbB receptor. In other situations, the molecule is one which does not significantly block ErbB ligand activation of an ErbB receptor. Further, the molecule may induce apoptosis, without inducing a large reduction in the percent of cells in S phase (e.g. one which only induces about 0-10% reduction in the percent of these cells relative to control).

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a molecule effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the molecule may prevent growth and/or kill existing cancer cells, it may be cytostatic and/or cytotoxic. For cancer therapy, efficacy can, for example, be measured by assessing the time to disease progression (TTP) and/or determining the response rate (RR).

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing" cancer or cancer comprising "ErbB-expressing cells" is a cancer comprising cells which have ErbB protein present at their cell surface. An "ErbB-expressing" cancer or cancer comprising "ErbB-expressing cells" is one which produces sufficient levels of ErbB2 at the surface of cells thereof, such that an anti-ErbB2 antibody can bind thereto and have a therapeutic effect with respect to the cancer.

A cancer "characterized by excessive activation" of an ErbB receptor is one in which the extent of ErbB receptor activation in cancer cells significantly exceeds the level of activation of that receptor in non-cancerous cells of the same tissue type. Such excessive activation may result from overexpression of the ErbB receptor and/or greater than normal levels of an ErbB ligand available for activating the ErbB receptor in the cancer cells. Such excessive activation may cause and/or be caused by the malignant state of a cancer cell.

A cancer which "overexpresses" an ErbB receptor is one which has significantly higher levels of an ErbB receptor, such as HER2, at the cell surface thereof, compared to a noncancerous cell of the same tissue type. Such overexpression may be caused by gene amplification or by increased transcription or translation. ErbB receptor overexpression may be determined in a diagnostic or prognostic assay by evaluating increased levels of the ErbB protein present on the surface of a cell (e.g. via an immunohistochemistry assay; IHC). Alternatively, or additionally, one may measure levels of ErbB-encoding nucleic acid in the cell, e.g. via fluorescent in situ hybridization (FISH; see WO98/45479 published October, 1998), Southern blotting, or polymerase chain reaction (PCR) techniques, such as real time quantitative PCR (RT-PCR). One may also study ErbB receptor overexpression by measuring shed antigen (e.g., ErbB extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

The tumors overexpressing HER2 may be rated by immunohistochemical scores corresponding to the number of copies of HER2 molecules expressed per cell, and can be determined biochemically: 0=0-10,000 copies/cell, 1+=at least about 200,000 copies/cell, 2+=at least about 500,000 copies/cell, 3+=at least about 2,000,000 copies/cell. Overexpression of HER2 at the 3+ level, which leads to ligand-independent activation of the tyrosine kinase (Hudziak et al., A., *Mol Cell Biol* 9(3):1165-72 (1989)), occurs in approximately 30% of breast cancers, and in these patients, relapse-free survival and overall survival are diminished (Slamon et al., *Science* 244(4905):707-12 (1989); Slamon et al., *Science* 235: 177-182 (1987)).

Conversely, a cancer which is "not characterized by overexpression of the ErbB2 receptor" is one which, in a diagnostic assay, does not express higher than normal levels of ErbB2 receptor compared to a noncancerous cell of the same tissue type.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK7; razoxane; sizofiran; spirogermanium; tenuazonic acid; triaziquone; 2,2',2'-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL$^7$, Bristol-Myers Squibb Oncology, Princeton, N.J.) and doxetaxel (TAXOTERE7, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

A "small molecule" is defined herein to have a molecular weight below about 500 Daltons.

2. Detailed Description

The present invention concerns antibody variants, preferably anti-HER2 antibody variants. The variant antibodies may take a number of different forms. For example, the antibodies may be, without limitation, intact antibodies, such as IgG1 antibodies, antibody fragments, such as a Fab, bispecific antibodies, humanized antibodies, or human antibodies.

The antibody variants preferably comprise one or more amino acid substitutions in the heavy chain variable domain and/or the light chain variable domain. More preferably, the antibody variants comprise one or more amino acid substitutions in the hypervariable regions of the heavy chain variable domain and/or the light chain variable domain.

While the present invention contemplates single amino acid substitutions according to the criteria herein, two or more substitutions may also be combined, e.g. from about two to about ten or about twenty substitutions per variable domain (i.e. up to about twenty or about forty, respectively, amino acid substitutions for both variable domains). The alterations described herein may be combined with other amino acid sequence alterations in the hypervariable regions or amino acid sequence alterations in other regions of the antibody.

Intact antibodies comprising the modified heavy and/or light chain domains described herein may be made by methods well known in the art. For example, recombinant variant antibodies may be produced in host cells such as *E. coli* cells, simian COS cells, Chinese Hamster Ovary (CHO) cells, or myeloma cells that do not otherwise produce antibody protein.

Alternatively, intact antibodies or antibody fragments can be isolated from antibody phage libraries generated using the techniques described, for example, in McCafferty et al., *Nature*, 348:552-554 (1990).

a. Humanized Antibodies

Methods for producing humanized antibodies, particularly humanized anti-HER2 antibodies are known. For example, production of a humanized anti-HER2 antibody known as hu4D5-8, are described, in the examples below and in U.S. Pat. No. 5,821,337, which is expressly incorporated herein by reference.

This antibody was derived from a murine monoclonal antibody, 4D5 (Fendly et al., *Cancer Res* 50(5):1550-8 (1990)), raised against the gene product of erbB2 known as p185$^{HER2}$ or HER2 (Slamon et al., *Science* 244(4905):707-12 (1989)). The murine monoclonal antibody 4D5 and its uses are described in PCT application WO 89106692 published Jul. 27, 1989. Murine antibody 4D5 was deposited with the ATCC and designated ATCC CRL 10463.

Both hu4D5 and 4D5 demonstrate antiproliferative activity against carcinoma cells overexpressing p185$^{HER2}$ (Carter et al., *Proc Natl Acad Sci USA* 89(10):4285-9 (1992b); Hudziak et al., *Mol Cell Biol* 9(3):1165-72 (1989)). The IgG form of hu4D5-8 (Herceptin R; trastuzumab) is used as a therapeutic in the treatment of breast cancer (reviewed by McKeage, K. & Perry, C. M., *Drugs* 62(1):209-43 (2002)).

In general, a humanized antibody preferably has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional confomational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Example 1 below describes production of an exemplary humanized anti-ErbB2 antibody. The humanized antibody herein may, for example, comprise nonhuman hypervariable region residues incorporated into a human variable heavy domain and may further comprise a framework region (FR) substitution at a position selected from the group consisting of R66($V_L$), A71($V_H$), T73($V_H$), A78($V_H$), and S93($V_H$) utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions R66($V_L$), A71($V_H$), T73($V_H$), A78($V_H$), and S93($V_H$).

b. Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589, 369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol.*

*Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human anti-ErbB2 antibodies are described in U.S. Pat. No. 5,772,997 issued Jun. 30, 1998 and WO 97/00271 published Jan. 3, 1997.

c. Antibody Fragments

Antibody fragments comprising the variant light and/or heavy chain variable domains described herein are contemplated. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)).

However, other techniques for the production of antibody fragments will be apparent to the skilled practitioner. For example, antibody fragments can now be produced directly by recombinant host cells. In one embodiment, the antibody fragments can be isolated from antibody phage libraries generated using the techniques described in McCafferty et al., *Nature*, 348:552-554 (1990). According to another approach, F(ab')$_2$ fragments can be isolated directly from recombinant host cell culture. Alternatively, Fab'-SH fragments can be directly recovered from *E. coli* and chemically coupled to form F(ab')$_2$ fragments (Carter et al., Bio/Technology 10:163-167 (1992)).

In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

d. Bispecific Antibodies

Bispecific antibodies that comprise the binding site of the anti-HER2 antibody variants described herein are contemplated. Bispecific antibodies are antibodies that have binding specificities for at least two different epitopes. Exemplary bispecific antibodies may bind to two different epitopes of the ErbB2 protein. Other such antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2. WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147: 60 (1991).

e. Amino Acid Sequence Modifications

Amino acid sequence modification(s) of the antibodies are contemplated. For example, it may be desirable to improve the binding affinity and/or other biological properties of an antibody. Amino acid sequence variants may be prepared by introducing appropriate nucleotide changes into the nucleic acid encodinrg the antibody variant, or by peptide synthesis. Such modifications include, for example, deletions from, and/or insertions into and/or substitutions of, residues within the amino acid sequences of the antibody variants. Any combination of deletion, insertion, and substitution is made to arrive at the final construct, provided that the final construct possesses the desired characteristics. The amino acid changes also may alter post-translational processing of the antibody variants, such as changing the number or position of glycosylation sites.

A useful method for identification of certain residues or regions of the antibodies that are preferred locations for mutagenesis is called "alanine scanning mutagenesis" as described by Cunningham and Wells, *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with a particular antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody variant with an N-terminal methionyl residue or the antibody fused to a cytotoxic polypeptide. Other insertional variants of the antibody molecule include the fusion of the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred conservative substitutions". If such substitutions result in a change in biological activity, then more substantial changes, denominated "exemplary substitutions" in Table 1, or as further described below in reference to amino acid classes, may be introduced and the products screened. The most preferred amino acid substitution variants are described in the examples below.

TABLE 1

| Original Residue | Exemplary Substitutions | Preferred Conservative Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Naturally occurring residues may be divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;

(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody variants also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) may be selected based on their biological properties. As such, variant(s) selected for further development may have improved biological properties relative to the parent antibody from which they are generated, such as enhanced binding affinity. A convenient way for generating such substitutional variants involves affinity maturation using phage display, discussed below.

It may also be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fe region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med*. 176:1191-1195 (1992) and Shopes, B., *J. Immunol*. 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

f. Affinity Maturation

Affinity maturation can produce antibodies with improved affinity, in comparison to the parent antibody. Sequence diversity in naturally occurring antibodies arises in B-cells with the recombination of selected diverse gene segments with imprecise cleavage events, nucleotide insertions, and secondary gene rearrangements, followed during maturation of the immunoglobulin response by secondary gene rearrangements and point mutations. These changes serve to enhance the specificity and effectiveness of the immune response through the selection of B-cell clones producing antibodies of increasing affinity and specificity.

The affinity maturation process has been effectively mimicked in vitro using antibody diversity libraries displayed on phage, yeast, or other hosts (reviewed by Hoogenboom, H. R. & Chames, P., *Immunol Today* 21(8):371-8 (2000); Maynard, J. & Georgiou, G., *Annu Rev Biomed Eng* 2:339-76 (2000); Rader, C. & Barbas, C. F., 3rd., *Curr Opin Biotechnol* 8(4): 503-8 (1997)). In particular, phage display can be performed in a variety of formats; for their review see, e.g. Johnson, Kevin S. and Chiswell, David J., *Current Opinion in Structural Biology* 3:564-571 (1993).

In one approach, nucleotide sequences coding for antibody hypervariable region sites of interest are mutated to generate all possible amino substitutions at each site. The mutated sequences are cloned in-frame into either a major or minor coat protein gene of a filamentous bacteriophage and displayed as functional antibody fragments on the surface of the phage particle.

The display is monovalent if a single antibody fragment is displayed per phage cell. Monovalent display can be accomplished with the use of phagemid and helper phage as described, for example, in Lowman, H. B., *Methods Mol Biol* 87:249-64 (1998). A preferred phage is M13 and display is preferably as a fusion protein with coat protein 3 as described in Lowman et. al., supra. Other suitable phage include fl and fd filamentous phage. Fusion protein display with other virus coat proteins is also known and may be used in this invention. See U.S. Pat. No. 5,223,409.

Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. In particular, the phage-displayed variants may be screened for their biological activity (e.g. binding affinity) as herein disclosed. Subsequent selection of variants with particular biological properties (e.g. high binding affinity) and continued rescreening of and reselection from the population of selected variants allows identification of variants with improvements in the biological activity screened for, such as increased affinity for a particular antigen.

Alanine scanning mutagenesis can be performed to identify candidate hypervariable region sites for modification. Those hypervariable region residues identified as contributing significantly to antigen binding are candidates for modification. Alternatively, or additionally, it may be beneficial to analyze a crystal structure of the antigen-antibody complex to identify contact points between the antibody and an antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development, as discussed above.

The process of affinity maturation can produce striking improvements in affinity compared to the parental antibody. A study in the mouse showed 10-10$^3$-fold improvements in $K_D$ during in vivo affinity maturation (Foote, J. & Milstein, C., *Nature* 352(6335):530-2 (1991)). Using a yeast-displayed scFv library, Wittrup and coworkers were able to improve the binding affinity of an antibody >1000-fold, to 48 fM ($K^D$=4.8×10$^{-14}$ M; (Boder et al., *Proc Natl Acad Sci USA* 97(20):10701-5 (2000)). Equally striking is the fact that a small number of mutations can sometimes affect these changes. For example, antigen-binding affinities were improved by 16-fold in a CDR-L3 point mutant of another anti-erbB2 antibody (Schier et al., *J Mol Biol* 263(4):551-67 (1996)), 14-fold in a CDR-H3 point mutant of an anti-VEGF (Chen et al., *J Mol Biol* 293(4):865-81 (1999)), and 8-fold in a CDR-H3 point mutant of an anti-gp120 antibody (Barbas et al., *Proc Natl Acad Sci USA* 91(9):3809-13 (1994)).

g. Screening for Antibodies with Desired Properties

After generating variant antibodies, one may further select those with particular biological characteristics, as desired.

For example, one may screen for antibodies with a desired binding affinity. As discussed below in the example, phage displayed Fab libraries may be sorted based on binding affinity. Briefly, antibody fragments derived from particular antibodies may be phage displayed and organized into libraries. The libraries may then be subjected to increasingly stringent rounds of antigen-binding selection using decreasing concentrations of antigen.

In addition, one may identify high affinity antibodies by determining the binding affinity and kinetics of a population of antibodies. In one embodiment, surface plasmon resonance (SPR) binding affinity measurements may be taken, as described in the examples below. Briefly, antibody fragments are derived from the antibodies of interest. A BIAcore-2000 or BIAcore-3000 real-time kinetic interaction analysis system (Biacore Inc., Piscataway, N.J.) may then be used to determine association ($k_{on}$) and dissociation ($k_{off}$) constants (Karlsson, R., Michaelsson, A. & Mattsson, L., *J Immunol Methods* 145(1-2):229-40 (1991)) of the antibody fragments in binding interactions with immobilized antigen, according the manufacture's instructions. An equilibrium constant, $K_D$, may be calculated from $k_{off}/k_{on}$, as known in the art. Free energy differences, as compared with wild-type antibody may be calculated as described (Wells, J. A., *Biochemistry* 29(37), 8509-17 (1990)): $\Delta\Delta G = -RT \ln(K_D^{(mutant)}/K_D^{(wild-type)})$.

Furthermore, in one embodiment, to identify growth inhibitory anti-ErbB2 antibodies, one may screen for antibodies which inhibit the growth of cancer cells which overexpress ErbB2. In one embodiment, a growth inhibitory antibody is able to inhibit growth of SK-BR-3 cells in cell culture by about 20-100% and preferably by about 50-100% at an antibody concentration of about 0.5 to 30 μg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 μg/ml of the anti-ErbB2 antibody is added per dish. After six days, the number of cells, compared to untreated cells are counted using an electronic COULTER™ cell counter. Those antibodies which inhibit growth of the SK-BR-3 cells by about 20-100%, and more preferably about 50-100% may be selected as growth inhibitory antibodies.

To select for variant antibodies which induce cell death, loss of membrane integrity as indicated by, e.g., PI, trypan blue or 7AAD uptake may be assessed relative to control. The preferred assay is the PI uptake assay using BT474 cells. According to this assay, BT474 cells (which can be obtained from the American Type Culture Collection (Rockville, Md.)) are cultured in Dulbecco's Modified Eagle Medium (D-MEM):Ham's F-12 (50:50) supplemented with 10% heat-inactivated FBS (Hyclone) and 2 mM L-glutamine. (Thus, the assay is performed in the absence of complement and immune effector cells). The BT474 cells are seeded at a density of $3 \times 10^6$ per dish in 100×20 mm dishes and allowed to attach overnight. The medium is then removed and replaced with fresh medium alone or medium containing 10 μg/ml of the appropriate monoclonal antibody. The cells are incubated for a 3 day time period. Following each treatment, monolayers are washed with PBS and detached by trypsinization. Cells are then centrifuged at 1200 rpm for 5 minutes at 4° C., the pellet resuspended in 3 ml ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

Antibodies which induce apoptosis may also be selected. An annexin binding assay using BT474 cells may be used to identify these antibodies. The BT474 cells are cultured and seeded in dishes as discussed in the preceding paragraph. The medium is then removed and replaced with fresh medium alone or medium containing 10 μg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 μg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies.

In addition to the annexin binding assay, a DNA staining assay using BT474 cells may be used to indentify antibodies that induce apoptosis. In order to perform this assay, BT474 cells which have been treated with the antibody of interest, as described in the preceding two paragraphs, are incubated with 9 μg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

In another embodiment, an antibody which blocks ligand activation of an ErbB receptor may be selected by determining the ability of the antibody to block ErbB ligand binding to cells expressing the ErbB receptor (e.g. in conjugation with another ErbB receptor with which the ErbB receptor of interest forms an ErbB hetero-oligomer). For example, cells naturally expressing, or transfected to express, ErbB receptors of the ErbB hetero-oligomer may be incubated with the antibody and then exposed to labeled ErbB ligand. The ability of the anti-ErbB2 antibody to block ligand binding to the ErbB receptor in the ErbB hetero-oligomer may then be evaluated.

For example, inhibition of HRG binding to MCF7 breast tumor cell lines by anti-ErbB2 antibodies may be performed using monolayer MCF7 cultures on ice in a 24-well-plate format essentially as described in Example 1 below. Anti-ErbB2 monoclonal antibodies may be added to each well and incubated for 30 minutes. $^{125}$I-labeled rHRGβ1$_{177-224}$ (25 pm) may then be added, and the incubation may be continued for 4 to 16 hours. Dose response curves may be prepared and an $IC_{50}$ value may be calculated for the antibody of interest. In one embodiment, the antibody which blocks ligand activation of an ErbB receptor will have an $IC_{50}$ for inhibiting HRG binding to MCF7 cells in this assay of about 50 nM or less, more preferably 10 nM or less. Where the antibody is an antibody fragment such as a Fab fragment, the $IC_{50}$ for inhibiting HRG binding to MCF7 cells in this assay may, for example, be about 100 nM or less, more preferably 50 nM or less.

Alternatively, or additionally, the ability of anti-ErbB2 antibody variants to block ErbB ligand-stimulated tyrosine phosphorylation of an ErbB receptor present in an ErbB hetero-oligomer may be assessed. For example, cells endogenously expressing the ErbB receptors or transfected to expressed them may be incubated with the antibody and then assayed for ErbB ligand-dependent tyrosine phosphorylation activity using an antiphosphotyrosine phosphotyrosine monoclonal antibody (which is optionally conjugated with a detectable label). The kinase receptor activation assay described in U.S. Pat. No. 5,766,863 is also available for determining ErbB receptor activation and blocking of that activity by an antibody.

In one embodiment, one may screen for an antibody which inhibits HRG stimulation of p180 tyrosine phosphorylation in MCF7 cells. For example, the MCF7 cells may be plated in 24-well plates and monoclonal antibodies to ErbB2 may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 µl of SDS sample buffer (5% SDS, 25 mM DTT, and 25 mM Tris-HCl, pH 6.8). Each sample (25 µl) may be electrophoresed on a 4-12% gradient gel (Novex) and then electrophoretically transferred to polyvinylidene difluoride membrane. Antiphosphotyrosine (at 1 µg/ml) immunoblots may be developed, and the intensity of the predominant reactive band at $M_r$~180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an $IC_{50}$ for the antibody of interest may be calculated. In one embodiment, the antibody which blocks ligand activation of an ErbB receptor will have an $IC_{50}$ for inhibiting HRG stimulation of p180 tyrosine phosphorylation in this assay of about 50 nM or less, more preferably 10 nM or less. Where the antibody is an antibody fragment such as a Fab fragment, the $IC_{50}$ for inhibiting HRG stimulation of p180 tyrosine phosphorylation in this assay may, for example, be about 100 nM or less, more preferably 50 nM or less.

One may also assess the growth inhibitory effects of an antibody on MDA-MB-175 cells, e.g, essentially as described in Schaefer et al., *Oncogene* 15:1385-1394 (1997). According to this assay, MDA-MB-175 cells may be treated with the anti-ErbB2 monoclonal antibody (10 µg/mL) for 4 days and stained with crystal violet. Incubation with an anti-ErbB2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5, both in the presence and absence of exogenous HRG.

In one embodiment, the anti-ErbB2 antibody variants of interest may block heregulin dependent association of ErbB2 with ErbB3 in both MCF7 and SK-BR-3 cells as determined in a co-immunoprecipitation experiment substantially more effectively than monoclonal antibody 4D5.

To screen for antibodies which bind to an epitope on ErbB2 bound by an antibody of interest, a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

The results obtained in the cell-based assays described above can then be followed by testing in animal, e.g. murine, models, and human clinical trials. In particular, the ability of an antibody variant to treat ErbB2 overexpressing tumors can be demonstrated in the transgenic mouse model disclosed in co-pending application Ser. No. 09/811115.

h. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, maytansinoids, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide). In a preferred embodiment, the antibody is conjugated to a maytansinoid as described in copending application Ser. No. 09/811123.

i. Pharmaceutical Formulations

Therapeutic formulations of the antibody variants used in accordance with the present invention are prepared by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized anti-ErbB2 antibody formulations are described in WO 97/04801, expressly incorporated herein by reference.

The formulation herein may also contain more than one active compound as necessary for the particular indication being treated, preferably those with complementary activities that do not adversely affect each other. For example, it may be desirable to further provide antibodies or antibody conjugates which bind to EGFR, ErbB2 (e.g. an antibody which binds a different epitope on ErbB2), ErbB3, ErbB4, or vascular endothelial factor (VEGF) in the one formulation. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

In one embodiment, the formulation comprises 5 mg/ml variant hu4D5-8, 100 mg/ml sucrose, 0.1% polysorbate 20 and 10 mM sodium succinate at pH 5.0.

Treatment with anti-ErbB2 antibody variants.

It is contemplated that, according to the present invention, anti-ErbB2 antibody variants may be used to treat various diseases or disorders. Exemplary conditions or disorders include benign or malignant tumors; leukemias and lymphoid malignancies; other disorders such as neuronal, glial, astrocytal, hypothalamic, glandular, macrophagal, epithelial, stromal, blastocoelic, inflammatory, angiogenic and immunologic disorders.

Generally, the disease or disorder to be treated is cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Preferably, antibody variants are used to treat breast cancer. The cancer will comprise ErbB-expressing cells, such that an anti-ErbB antibody herein is able to bind to the cancer, and will be typically characterized by overexpression of the ErbB receptor. In a preferred embodiment, the cancer comprises ErbB2-expressing cells, even more preferably, cells which are characterized by overexpression of the ErbB2 receptor. To determine ErbB, e.g. ErbB2 expression in the cancer, various diagnostic/prognostic assays are available. In one embodiment, ErbB2 overexpression may be analyzed by immunohistochemistry (IHC), e.g. using the HERCEPTEST® (Dako). Parrafin embedded tissue sections from a tumor biopsy may be subjected to the IHC assay and accorded a ErbB2 protein staining intensity criteria as follows:

| | |
|---|---|
| Score 0 | no staining is observed or membrane staining is observed in less than 10% of tumor cells. |
| Score 1+ | a faint/barely perceptible membrane staining is detected in more than 10% of the tumor cells. The cells are only stained in part of their membrane. |
| Score 2+ | a weak to moderate complete membrane staining is observed in more than 10% of the tumor cells. |
| Score 3+ | a moderate to strong complete membrane staining is observed in more than 10% of the tumor cells. |

Those tumors with 0 or 1+ scores for ErbB2 overexpression assessment may be characterized as not overexpressing ErbB2, whereas those tumors with 2+ or 3+ scores may be characterized as overexpressing ErbB2.

Alternatively, or additionally, fluorescence in situ hybridization (FISH) assays such as the INFORM™ (sold by Ventana, Ariz.) or PATHVISION™ (Vysis, Ill.) assays may be carried out on formalin-fixed, paraffin-embedded tumor tissue to determine the extent (if any) of ErbB2 overexpression in the tumor. In comparison with the IHC assay, the FISH assay, which measures her2 gene amplification, seems to correlate better with response of patients to treatment with anti-HER2 antibodies, and is currently considered to be the preferred assay to identify patients likely to benefit from anti-HER2 antibody treatment (e.g. treatment with commercially available HERCEPTIN®) or treatment with the variants of the present invention.

Preferably, the variants of the present invention and/or the ErbB, e.g. ErbB2, protein to which they are bound are internalized by the cell, resulting in increased therapeutic efficacy of the variant in killing the cancer cell to which they bind. In a preferred embodiment, a cytotoxic agent, such as a maytansinoid, targets or interferes with nucleic acid in the cancer cell.

The anti-ErbB antibody variants are administered to a mammal, preferably to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Other therapeutic regimens may be combined with the administration of the anti-ErbB antibody variants. The combined administration includes coadministration, using separate formulations or a single pharmaceutical formulation, and consecutive administration in either order, wherein preferably there is a time period while both (or all) active agents simultaneously exert their biological activities.

In one embodiment, the patient is treated with two or more different anti-ErbB antibodies, at least one of which is in the form of a variant. For example, the patient may be treated with a first anti-ErbB2 antibody variant in which the antibody is growth inhibitory, and a second anti-ErbB2 antibody or antibody-immunoconjugate, e.g. an antibody-maytansinoid conjugate, which blocks ligand activation of an ErbB receptor (e.g. 2C4 or a humanized and/or affinity matured variant thereof) or induces apoptosis of an ErbB2-overexpressing cell (e.g. 7C2, 7F3 or humanized and/or affinity matured variants thereof). In another embodiment, the treatment involves the administration of antibodies that specifically bind two or more different ErbB receptors, such as, for example, ErbB2 and EGFR receptors, where at least one of the anti-ErbB antibodies is a hu4D5-8 variant. Preferably such combined therapy results in a synergistic therapeutic effect.

It may also be desirable to combine administration of the anti-ErbB antibody variants, with administration of an antibody directed against another tumor-associated antigen, which is not member of the ErbB family of receptors. The other antibody in this case may, for example, bind to vascular endothelial growth factor (VEGF), and may be in the form of a maytansinoid conjugate, or another immunoconjugate.

In one embodiment, the treatment of the present invention involves the combined administration of an anti-ErbB2 antibody variant (or variants) and one or more chemotherapeutic agents or growth inhibitory agents, including coadministration of cocktails of different chemotherapeutic agents. Preferred chemotherapeutic agents include taxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In a preferred embodiment, the treatment is initiated with an anti-ErbB antibody variant, followed by maintenance treatment with an parental anti-ErbB antibody.

The antibody variants may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient.

Sometimes, it may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the agent and anti-ErbB2 antibody.

For the prevention or treatment of disease, the appropriate dosage of an antibody variant will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody variant is suitably administered to the patient at one time or over a series of treatments. For repeated administrations over several days or longer, depending on the condition, the treatment is sustained until a desired suppression of disease symptoms occurs. The progress of this therapy is easily monitored by conventional techniques and assays.

j. Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an antibody variant, according to the present teachings. In one embodiment, the container is a 10 cc vial containing 10 mL of a solution comprising an antibody variant described herein.

The label or package insert indicates that the composition is used for treating the condition of choice, such as cancer. In a preferred embodiment the label or package inserts indicate that the composition is used for treating breast cancer. In another embodiment, the label or package inserts indicates that the composition comprising a variant antibody which binds ErbB2 can be used to treat cancer which expresses an ErbB receptor selected from the group consisting of epidermal growth factor receptor (EGFR), ErbB2, ErbB3 and ErbB4, preferably EGFR. In addition, the label or package insert may indicate that the patient to be treated is one having cancer characterized by excessive activation of an ErbB receptor selected from EGFR, ErbB2, ErbB3 or ErbB4. For example, the cancer may be one which overexpresses one of these receptors and/or which overexpresses an ErbB ligand (such as TGF-α). The label or package insert may also indicate that the composition can be used to treat cancer, wherein the cancer is not characterized by overexpression of the ErbB2 receptor. In other embodiments, the package insert may indicate that the composition can also be used to treat hormone independent cancer, prostate cancer, colon cancer or colorectal cancer.

Moreover, the article of manufacture may comprise (a) a first container with a composition contained therein, wherein the composition comprises an antibody variant which binds ErbB2 and inhibits growth of cancer cells which overexpress ErbB2; and (b) a second container with a composition contained therein, wherein the composition comprises a second antibody which binds ErbB2 and blocks ligand activation of an ErbB receptor, or a conjugate of this second antibody with a maytansinoid. The article of manufacture in this embodiment of the invention may further comprise a package insert indicating that the first and second compositions can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated in the following non-limiting examples.

EXAMPLE 1

Production, Characterization and Humanization of Anti-ErbB2 Monoclonal Antibody 4D5

The murine monoclonal antibody 4D5 which specifically binds the extracellular domain of ErbB2 was produced as described in Fendly et al., *Cancer Res* 50(5):1550-8 (1990). Briefly, NIH 3T3/HER2-3$_{400}$ cells (expressing approximately 1×10$^5$ ErbB2 molecules/cell) produced as described in Hudziak et al., *Mol Cell Biol* 9(3):1165-72 (1989) were harvested with phosphate buffered saline (PBS) containing 25 mM EDTA and used to immunize BALB/c mice. The mice were given injections i.p. of 10$^7$ cells in 0.5 ml PBS on weeks 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653. Hybridoma supernatants were screened for ErbB2-binding by ELISA and radioimmunoprecipitation.

Epitope Mapping and Characterization

The ErbB2 epitope bound by monoclonal antibody 4D5 was determined by competitive binding analysis (Fendly et al., *Cancer Res* 50(5):1550-8 (1990)). Cross-blocking studies were done by direct fluorescence on intact cells using the PANDEX™ Screen Machine to quantitate fluorescence. The monoclonal antibody was conjugated with fluorescein isothiocyanate (FITC), using established procedures (Wofsy et al. *Selected Methods in Cellular Immunology*, p. 287, Mishel and Schiigi (eds.) San Francisco: W. J. Freeman Co. (1980)). Confluent monolayers of NIH 3T3/HER2-3$_{400}$ cells were trypsinized, washed once, and resuspended at 1.75×10$^6$ cell/ml in cold PBS containing 0.5% bovine serum albumin (BSA) and 0.1% NaN$_3$. A final concentration of 1% latex particles (IDC, Portland, Oreg.) was added to reduce clogging of the PANDEX™ plate membranes. Cells in suspension, 20 µl, and 20 µl of purified monoclonal antibodies (100 µg/ml to 0.1 µg/ml) were added to the PANDEX™ plate wells and incubated on ice for 30 minutes. A predetermined dilution of the FITC-labeled monoclonal antibody in 20 µl was added to each well, incubated for 30 minutes, washed, and the fluorescence was quantitated by the PANDEX™. Monoclonal antibodies were considered to share an epitope if each blocked binding of the other by 50% or greater in comparison to an irrelevant monoclonal antibody control. In this experiment, monoclonal antibody 4D5 was assigned epitope I (amino acid residues from about 529 to about 625, inclusive, within the ErbB2 extracellular domain (residues 22 to about 645, inclusive).

The murine monoclonal anti-HER2 antibody 4D5 inhibits the growth of breast cancer cell lines. The growth inhibitory characteristics of monoclonal antibody 4D5 were evaluated using the breast tumor cell line, SK-BR-3 (see Hudziak et al., *Mol Cell Biol* 9(3):1165-72 (1989)). Briefly, SK-BR-3 cells were detached by using 0.25% (vol/vol) trypsin and suspended in complete medium at a density of 4×10$^5$ cells per ml. Aliquots of 100 µl (4×10$^4$ cells) were plated into 96-well microdilution plates, the cells were allowed to adhere, and 100 µl of media alone or media containing monoclonal antibody (final concentration 5 µg/ml) was then added. After 72 hours, plates were washed twice with PBS (pH 7.5), stained with crystal violet (0.5% in methanol), and analyzed for relative cell proliferation as described in Sugarman et al. *Science* 230:943-945 (1985). Monoclonal antibody 4D5 inhibited SK-BR-3 relative cell proliferation by about 56%.

Monoclonal antibody 4D5 was also evaluated for its ability to inhibit HRG-stimulated tyrosine phosphorylation of proteins in the M$_r$ 180,000 range from whole-cell lysates of MCF7 cells (Lewis et al. *Cancer Research* 56:1457-1465 (1996)). MCF7 cells are reported to express all known ErbB receptors, but at relatively low levels. Since ErbB2, ErbB3, and ErbB4 have nearly identical molecular sizes, it is not possible to discern which protein is becoming tyrosine phosphorylated when whole-cell lysates are evaluated by Western blot analysis. However, these cells are ideal for HRG tyrosine phosphorylation assays because under the assay conditions used, in the absence of exogenously added HRG, they exhibit low to undetectable levels of tyrosine phosphorylation proteins in the M$_r$ 180,000 range.

MCF7 cells were plated in 24-well plates and monoclonal antibodies to ErbB2 were added to each well and incubated for 30 minutes at room temperature; then rHRGβ1$_{177-244}$ was added to each well to a final concentration of 0.2 nM, and the incubation was continued for 8 minutes. Media was carefully aspirated from each well, and reactions were stopped by the addition of 100 µl of SDS sample buffer (5% SDS, 25 mM DTT, and 25 mM Tris-HCl, pH 6.8). Each sample (25 µl) was electrophoresed on a 4-12% gradient gel (Novex) and then electrophoretically transferred to polyvinylidene difluoride membrane. Antiphosphotyrosine (4G10, from UBI, used at 1 µg/ml) immunoblots were developed, and the intensity of the predominant reactive band at M$_r$-180,000 was quantified by reflectance densitometry, as described previously (Holmes et al. *Science* 256:1205-1210 (1992); Sliwkowski et al. *J. Biol. Chem.* 269:14661-14665 (1994))

Monoclonal antibody 4D5 significantly inhibited the generation of a HRG-induced tyrosine phosphorylation signal at M$_r$ 180,000. In the absence of HRG, but was unable to stimulate tyrosine phosphorylation of proteins in the M$_r$ 180,000 range. Also, this antibody does not cross-react with EGFR (Fendly et al., *Cancer Res* 50(5):1550-8 (1990)), ErbB3, or ErbB4. Monoclonal antibody 4D5 was able to block HRG stimulation of tyrosine phosphorylation by −50%.

The growth inhibitory effect of monoclonal antibody 4D5 on MDA-MB-175 and SK-BR-3 cells in the presence or absence of exogenous rHRGβ1 was assessed (Schaefer et al., *Oncogene* 15:1385-1394 (1997)). ErbB2 levels in MDA-MB-175 cells are 4-6 times higher than the level found in normal breast epithelial cells and the ErbB2-ErbB4 receptor is constitutively tyrosine phosphorylated in MDA-MB-175 cells. Monoclonal antibody 4D5 was able to inhibit cell proliferation of MDA-MB-175 cells, both in the presence and absence of exogenous HRG. Inhibition of cell proliferation by 4D5 is dependent on the ErbB2 expression level (Lewis et al., *Cancer Immunol. Immunother.* 37:255-263 (1993)). A maximum inhibition of 66% in SK-BR-3 cells could be detected. However this effect could be overcome by exogenous HRG.

Humanization

The murine monoclonal antibody 4D5 was humanized, using a novel "gene conversion mutagenesis" strategy, as described in U.S. Pat. No. 5,821,337, the entire disclosure of which is hereby expressly incorporated by reference. The humanized monoclonal antibody 4D5 used in the following experiments is the antibody variant designated as hu4D5-8 in that patent. Hu4D5-8 comprises a light chain variable domain ($V_L$) (SEQ ID NO: 1), and a heavy chain variable domain ($V_H$) (SEQ ID NO: 2). Within the light chain variable domain of SEQ ID NO:1 are three hypervariable regions: $V_L$-hypervariable region 1, comprising amino acids RASQDVNTAVA (SEQ ID NO: 19); $V_L$-hypervariable region 2 comprising amino acids SASFLYS (SEQ ID NO: 20); and $V_L$-hypervariable region 3 comprising amino acids QQHYTTPPT (SEQ ID NO: 21). Similarly, there are three hypervariable regions within the heavy chain variable domain of SEQ ID NO: 2: $V_H$-hypervariable region 1 comprising amino acids GFNIKDTYIH (SEQ ID NO: 22), $V_H$-hypervariable region 2 comprising amino acids RIYPTNGYTRYADSVKG (SEQ ID NO: 23); and $V_H$-hypervariable region 3 comprising amino acids WGGDGFYAMDY (SEQ ID NO: 24).

EXAMPLE 2

HU4D5-8 Variants

Figure 1B:
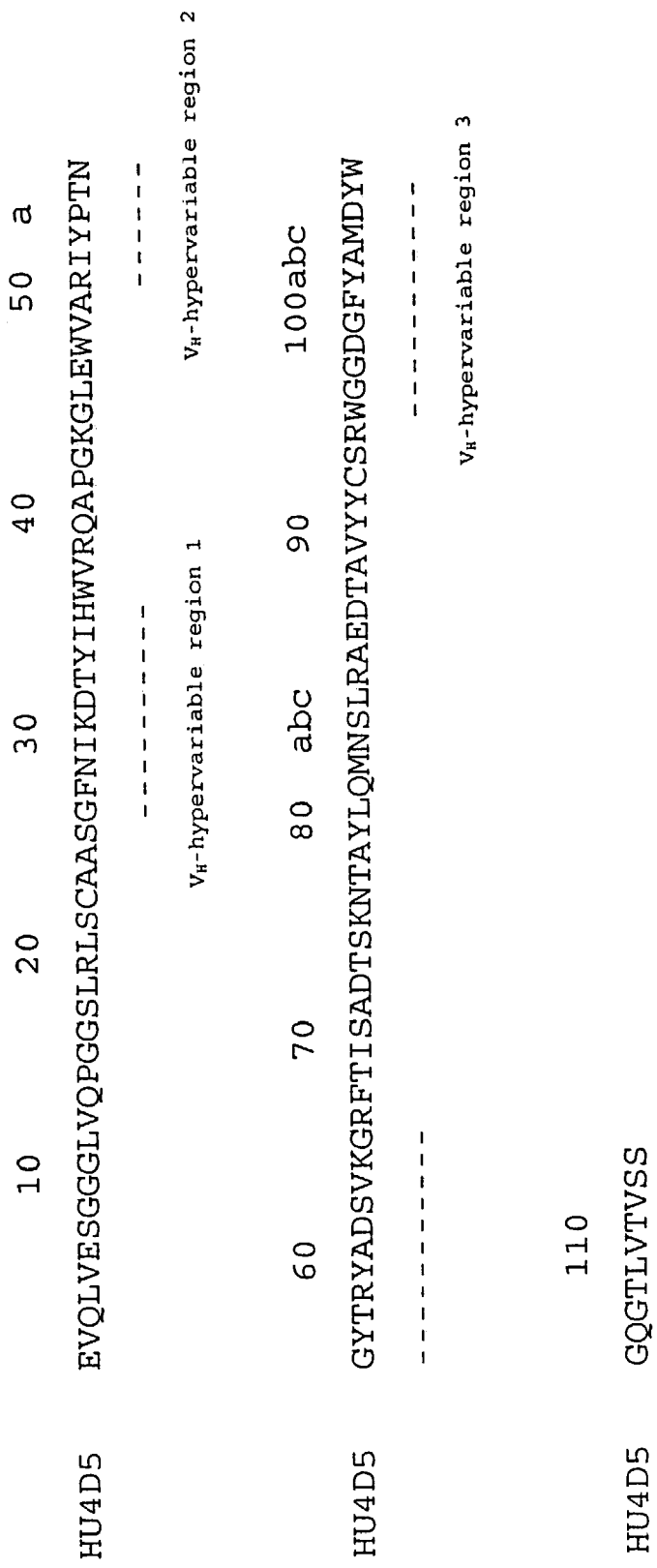
FIG. 1B shows the heavy chain variable domain ($V_H$) amino acid residues of huMAb4D5-8 (SEQ ID NO. 2). Both FIGS. 1A and 1B use the generally accepted numbering scheme from Kabat, E. A., et al., *Sequences of Proteins of Immunological Interest* (National Institutes of Health, Bethesda, Md. (1987)).

Recognition of an antibody often involves a subset of the hypervariable region residues with contacts at the center of the antigen-combining site (see Schier et al., *J Mol Biol* 263(4):551-67 (1996)). This is the case in the recognition of the tumor antigen HER2 by the humanized antibody known as hu4D5. Phage display allowed exploration of the overall variability of the binding site, revealing positions at which further substitutions might be made to improve affinity. The amino acid sequences of the light and heavy chains of hu4D5-8, along with CDR residues, are shown in FIGS. 1A and 1B, respectively.

Sequence variability within the high-affinity HER2-binding site of the hu4D5-8 antibody was tested by constructing monovalently displayed Fab-phage libraries, selecting for HER2 binding clones, and sequencing a large sample (50-70 clones) from each library pool at a point in the selection process where a high level of overall diversity (minimal siblings, that is occurrence of identical clones) was observed.

Selection of CDR Residues for Substitutions

Figures 2A, 2B:
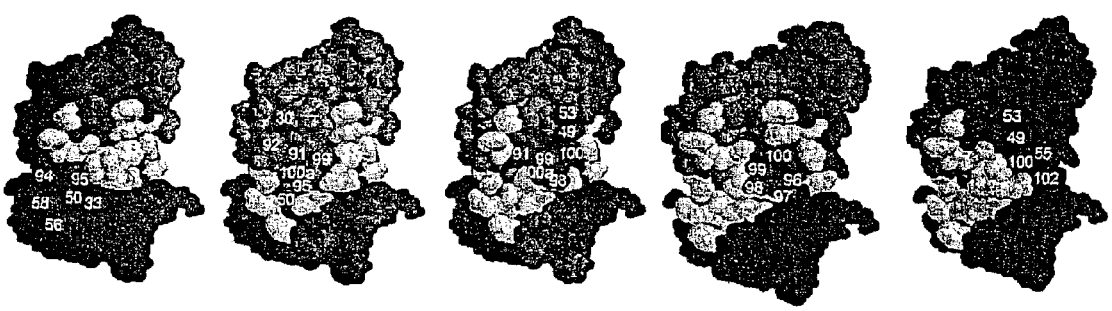
FIG. 2A shows the residue positions mutated in phage displayed libraries. Nineteen residues on the surface of the hu4D5-8 Fab were fully randomized using NNS codon degeneracy. The randomized residues (Kabat numbering; Johnson, G. & Wu, T. T., *Nucleic Acids Res* 29(1):205-6 (2001)) were grouped by their location on the surface of the antibody structure into five libraries, shown in FIG. 2B. Some residues were included in more than one library to test for context-dependent effects.

Design of the phage libraries centered on four key residues from an alanine scan study (Kelley, R. F. & O'Connell, M. P., *Biochemistry* 32(27):6828-35 (1993)). These included CDR residues both in the light-chain ($V_L$) and in the heavy-chain ($V_H$) variable domains: H91($V_L$), R50($V_H$), W95($V_H$), and Y100a($V_H$) (Kelley, R. F. & O'Connell, M. P., *Biochemistry* 32(27):6828-35 (1993)). Also selected for substitutions were additional surface-exposed residues that were proximal to the $V_L$:$V_H$ interface, near the center of the antigen combining site, based on inspection of the hu4D5-8 crystal structure (Eigenbrot et al., *J Mol Biol* 229(4):969-95 (1993)). Residues known to be important for the main chain conformation, or canonical structure, (Chothia et al., *Nature* 342(6252):877-83 (1989)) were omitted from the libraries. In order to achieve adequate representation of all variants, the targeted positions were divided into five libraries, each consisting of a small cluster of surface positions, with no more than seven residues targeted in each. Each library, except for one targeting five residues in CDR-H3, allowed variation of residues from both $V_L$ and $V_H$ (FIG. 2). Some residues were represented in more than one library in order to test for context effects and allow for covariation with other proximal positions.

Oligonucleotides for Use in Site-Directed Mutagenesis

A total of 19 residues of hu4D5-8 were randomized using site-directed mutagenesis with degenerate NNS codons (N=A, G, T or C; S=G or C) that encode all 20 amino acids. Site-directed mutagenesis was carried out using the following deoxyoligonucleotides: Lib1.1 GCC AGT CAG GAT GTG NNS ACT GCT GTA GCC TGG (SEQ ID NO: 3); Lib1.2 CT TAT TAC TGT CAG CAA NNS NNS ACT ACT CCT CCC ACG (SEQ ID NO: 4); Lib1.3 C CTG GAA TGG GTT GCA NNS ATT TAT CCT ACG AAT GG (SEQ ID NO: 5); Lib1.4 C TAT TAT TGT TCT AGA NNS GGA GGG GAC NNS TTC NNS GCT ATG GAC TAC TGG GG (SEQ ID NO: 6); Lib2.1 CCG AAA CTA CTG ATT NNS TCG GCA TCC NNS CTC TAC TCT GGA GTC (SEQ ID NO: 7); Lib2.2 C GCA ACT TAT TAC TGT CAG CAA NNS TAT ACT ACT CCT CCC (SEQ ID NO: 8); Lib2.3 GT TCT AGA TGG GGA GGG NNS NNS NNS NNS GCT ATG GAC TAC TGG G (SEQ ID NO: 9); Lib3.1 C AAC ATT AAA GAC ACC NNS ATA CAC TGG GTG CGT C (SEQ ID NO: 10); Lib3.2 G GGC CTG GAA TGG GTT GCA NNS ATT TAT CCT ACG AAT GGT NNS ACT NNS TAT GCC GAT AGC G (SEQ ID NO: 11); Lib3.3 C TAT TAT TGT TCT AGA NNS GGA GGG GAC GGC TTC (SEQ ID NO: 12); Lib3.4 CAG CAA CAT TAT ACT NNS CCT CCC ACG TTC GGA CA (SEQ ID NO: 13); Lib4.1 G CGT GCT GAG GAC ACT GCC GTC TAT TAT TGT TCT AGA TGG NNS NNS NNS NNS NNS TAT GCT ATG GAC TAC TGG GGT CAA GG (SEQ ID NO: 14); Lib5.1 CCG AAA CTA CTG ATT NNS TCG GCA TCC NNS CTC NNS TCT GGA GTC CCT TCT CGC (SEQ ID NO: 15); Lib5.2 GG GGA GGG GAC GGC NNS TAT GCT ATG GAC NNS TGG GGT CAA GGA ACC (SEQ ID NO: 16).

Oligonucleotides used to sequence the selected phage were TGT AAA ACG ACG GCC AGT CCG TTT AGG TGT TTT CAC GAG CAC T (SEQ ID NO: 17) and CAG GAA ACA GCT ATG ACC GTT CCA CGA CAC CGT CAC CGG TTC (SEQ ID NO: 18).

Construction of hu4D5-8 Phase Libraries

The hu4D5-8 phagemid (564/11) was made by fusing the light and heavy chains of the Fab (Kelley et al., *Biochemistry* 31(24):5434-41 (1992)) to a truncated form of g3, encoding one of the M13 phage coat proteins.

The hu4D5 libraries were constructed as described in previous methods (Sidhu et al., *Methods Enzymol* 328: 333-63 (2000a); Lowman, H. B., *Methods Mol Biol* 87:249-64 (1998)). For each library, the template was a modified version of phagemid 564/11 that contained stop codons (TAA) introduced at positions where amino acids were to be mutated. A different stop template was made for each library. The stop templates and mutagenic oligos described in the previous section were used in standard Kunkel mutagenesis (Kunkel et al., *Methods Enzymol* 204:125-39 (1991)). Annealing of mutagenic oligos to the stop template repaired the stop codon and introduced the desired mutations. All libraries were on the order of $10^{10}$, well beyond the theoretical diversities by 10 to 1000-fold. This ensured that at least one copy of all mutations was present in each library.

Sorting of hu4D5-8 Phage Libraries

Phage were amplified in *E.coli* and subjected to increasingly stringent rounds of antigen-binding selection using decreasing concentrations of HER2-ECD, starting at 10 nM and decreasing 10-fold in each round.

The phage libraries were selected by their ability to bind to the HER2 receptor using a strategy similar to that previously described (Hawkins et al., *J Mol Biol* 226(3):889-96 (1992)). Library phage that bound to biotinylated HER2-ECD antigen were captured with magnetic beads that had been blocked with milk protein for 1 hour at 37° C. A preincubation of phage with beads for 1 hour at 37° C. minimized nonspecific binding of the phage selected in each round. The beads bound to HER2-phage complexes were separated and washed five times during round 1, and 10 times for all subsequent rounds of sorting. Phage were eluted from the beads and neutralized with HCl. A portion of the eluted phage were propagated in rapidly dividing XL-1 (Stratagene, La Jolla, Calif.) or SS320 (Sidhu et al., *Methods Enzymol* 328: 333-63 (2000b)) cells in the presence of M13-VCS (Stratagene). Library size was determined by plating serial dilutions of cells onto agar. Library enrichment was determined by comparing the number of phage isolated in the presence and in the absence of antigen. Phage were otherwise treated identically with regard to pre-incubation, separation by magnetic beads, and wash steps.

In the initial round of selection, $1 \times 10^{13}$ of library phage were incubated with 10 nM antigen. The antigen concentration was then decreased 10-fold during each subsequent round of screening. The phage supernatants of individual clones were assayed for activity in a phage ELISA (Lowman, H. B., *Methods Mol Biol* 87:249-64 (1998)) and showed that more than 50% were positive after the second round of selection. All libraries displayed enrichment by round 4, with selection using 0.01 nM antigen.

Sequencing and Analysis of Phase DNA

Phage were sequenced directly from cell-culture supernatants. A standard PCR reaction of the phage amplified the light and heavy chain of the Fab. The forward and reverse M13 universal primer sequence was included in the PCR primers so that the product could be easily sequenced with standard primers. The sequences obtained were first analyzed in the program SGcount as previously described (Weiss et al., *Proc Natl Acad Sci USA* 97(16), 8950-4 (2000)). Clones with sequence uncertainties were removed from the analysis. The remaining sequences were then filtered by (1) removing siblings, (2) normalizing for any codon bias that resulted from the use of an NNS codon, and (3) normalizing for the total number of sequences, so that the results from different libraries could be directly compared. The number of clones analyzed for each library was as follows: 71 from library-1, 82 from library-2, 71 from library-3, 74 from library-4, and 57 from library-5.

Analysis of Variability within the Binding Site of hu4D5-8

In order to map sequence variability within the binding site of hu4D5-8 systematically, the Wu-Kabat variability coefficient from the sequence data was calculated. Variability ($V_S$) is the number of different amino acids at a given position divided by the frequency of the most common amino acid at that position (Wu, T. T. & Kabat, E. A., *J Exp Med* 132(2), 211-50 (1970)).

Clones from each library were sequenced after 4 rounds of HER2-ECD selection. Sequence data was normalized to adjust for codons that were represented more than once. In most libraries there were few siblings (clones with identical DNA sequence). However, library-4 was dominated by a single sequence with only 7 unique sequences total, and since all but two residues in library-4 were mutated elsewhere, it was omitted from further analysis. Any siblings in the remaining libraries were also omitted in the analysis of amino acid variability.

Figure 5:
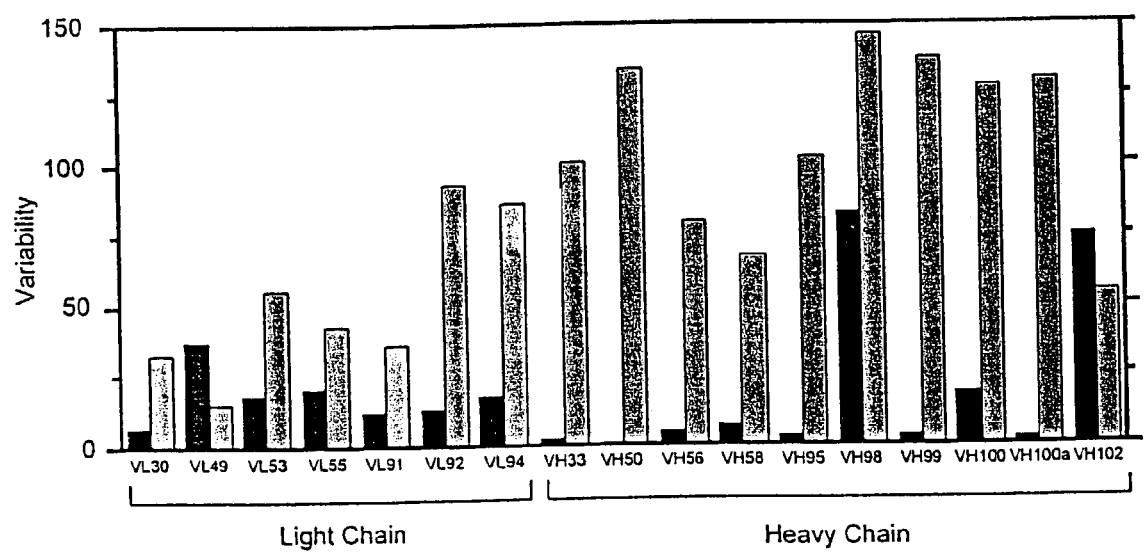
FIG. 5 shows the variability of selected residues in hu4D5-8. The Wu-Kabat variability parameter ($V_S$) for the phage selected results (solid) versus the natural variability of human Kappa light chains and human heavy chains (gray). Variability is calculated as follows: $V_S = n_{aa}/(N_{max}/N_{total})$ where $n_{aa}$=the number of different amino acids (i.e. of the 20 possible) at a given position, $N_{max}$=occurrences of the most common amino acid at that position, and $N_{total}$=total number of amino acids at that position (Wu, T. T. & Kabat, E. A., *J Exp Med* 132(2), 211-50 (1970)).

Using this measure, the variability of phage selected amino acids could be compared to the natural variability of roughly 2000 human Ig κ light chains and 4500 human Ig heavy chains found in the Kabat database (Johnson, G. & Wu, T. T., *Nucleic Acids Res* 29(1):205-6 (2001)). The results (FIG. 5) showed extremely diminished variability in the hu4D5-8 residues as compared with variability of a wide range of antibodies in the Kabat database. However, within the hu4D5-8 binding site, there are clearly differences in variability of the residues examined here. These positions were ranked according to their variability score: Class 1, relatively invariant residues ($V_S<10$); Class 2, moderately variable residues ($V_S$ 10 to 40); and Class 3, highly variable residues ($V_S>40$). Sequence information for clones selected from the four libraries is shown in FIG. 3, presented according to this classification system. All amino acids were observed at some frequency and position, but Cys and Gln were only rarely observed (2-3% at two positions each). Also studied was the relationship between the patterns of variability and the effects of substitutions on binding affinity.

Overall, wild-type residues were strongly conserved at many positions. Heavy-chain residues Y33, R50, Y56, R58, W95, G99, F100, and Y100a along with light-chain residues F53 and T94, were all conserved with normalized frequencies $\geq 45\%$ (FIG. 3). Y100a($V_H$), a >12,000-fold effect when mutated to Ala (Kelley, R. F. & O'Connell, M. P., *Biochemistry* 32(27):6828-35 (1993)), R50($V_H$), a >2000-fold effect when mutated to Ala, and G99($V_H$), not previously mutated, were about 90-100% conserved the latter two in two independent libraries. On the other hand, some of the residues appearing in multiple libraries did show context-dependent differences in amino acid occurrences. W95($V_H$), a >18,000-fold Ala hit, showed wild-type as the preferred residue with 82% frequency in one library (library 2), but with only 59% in another (library 1). F100($V_H$), a modest 7-fold Ala hit, was rather strongly conserved in one library (library 3), but approximately equally often substituted by Trp or Met in another (library 5). F53 ($V_L$) is another example of how some selected residues varied with context. In library 3, the wild-type Phe was preferred by 67% to 16% over Trp, while in library 5, the preference was reversed with Trp favored over Phe by 55% to 16% (FIG. 3).

Wild-type residues were not so predominant at other positions. Interestingly, at T94($V_L$), where Ala substitution had little effect, there was a 45% conservation of Thr, but also a rather high occurrence (27%) of a chemically distinct substitution, Trp. Several light-chain residues that had shown a range of Ala-scan effects from 6-fold to 200-fold also showed strong selection ($\geq 45\%$ frequency) of non-wild-type residues, but preserved the wild-type chemical character: N30 ($V_L$), Y55($V_L$), H91($V_L$) in two libraries, and Y92($V_L$). At $V_L$30 the wild-type Asn occurred in only 34% of the selected clones and was replaced with Ser in 53% of the selected clones. Interestingly, at the neighboring $V_L$92, Trp occurred in 41% of the selected clones, while Met, Phe, and Tyr (wild-type) each occurred in 16-19% of the clones. The Tyr at $V_L$55 was preferably substituted by Trp (58%) and less frequently by Phe or Tyr (12% each). Because these types of substitution in general had unpredictable effects on binding affinity, they were examined further (see below) as point mutations in the context of soluble hu4D5-8 Fab preparations.

At the remaining three positions, Y49($V_L$), D98($V_H$), and Y102($V_H$), the pattern of substitutions were more complex, with no single amino acid occurring with more than about 30% frequency. These residues retained WT identity with frequency <10% and had the largest variety of amino acids. Y49($V_L$) (along with Y55($V_L$) faced $V_H$100 and $V_H$102 at the light-chain:heavy-chain interface. $V_H$49 was poorly conserved (only 9% WT) in two libraries and showed a preference for Trp or Phe, depending on the context. The Tyr at $V_H$102 was a side chain from the murine CDR that was added during humanization (Carter et al., *Proc Natl Acad Sci USA* 89(10):4285-9 (1992b)) to improve binding affinity; however, the point mutation in isolation did not affect affinity (Kelley, R. F. & O'Connell, M. P., *Biochemistry* 32(27):6828-35 (1993)). From the phage library data, the human framework residue, Val was actually preferred at this position. Both Val and Tyr often occur in human Ig heavy chains at this location (Johnson, G. & Wu, T. T., *Nucleic Acids Res* 29(1):205-6 (2001)). A neighboring residue, $V_L$55, was poorly conserved (mentioned above). The most poorly conserved residue was $V_H$98. D98($V_H$) is located in the tip of variable loop 3 of the heavy chain. It was mutated in 98% of all selected clones and substitution of every amino acid except Cys was observed there. The most frequent amino acid at this position was Trp, occurring with 23% frequency. These substitutions were also of particular interest, and they are examined further (see below) as point mutations in the context of soluble hu4D5-8 Fab preparations.

Comparison of Sequence Variability and Ala Scan Data

An alanine scan replaces WT residues with alanine and generally measures loss of function. A goal for the phage libraries used in these experiments was to maintain function through random substitutions and antigen-binding selection. The degree of sequence variation using the $V_S$ parameter (FIG. 5) with the Ala-scan map (Kelley, R. F. & O'Connell, M. P., *Biochemistry* 32(27):6828-35 (1993)) of hu4D5-8 in the context of the crystal structure of the antibody (FIG. 7) were compared. The two maps showed some common and some distinct features.

Four residues of hu4D5-8 had been found to be most critical for antigen binding in the binding site of HER2-ECD based on alanine mutagenesis (Kelley, R. F. & O'Connell, M. P., *Biochemistry* 32(27):6828-35 (1993)). The importance of three of these residues (see FIG. 7), R50($V_H$), W95($V_H$), and Y100a($V_H$), was confirmed in that they were consistently selected as their WT identity despite the context in which they were randomized. However, phage display also selected four additional residues (N30($V_L$), R56($V_H$), R58($V_H$), and G99($V_H$)) that are highly conserved as WT that were not detected by alanine scanning (FIG. 7). Two of these, N30($V_L$) and R56($V_H$), were found to decrease $K_D$ by 4 to 6-fold when mutated to alanine.

One discrepancy between the alanine scan and phage display results was $V_L$91. When $V_L$91 was mutated to alanine there was a 200-fold decrease in binding. $V_L$91 was mutated to a Phe in 44-45% of all selected clones in two different libraries. WT hu4D5-8 has a His in this position. While this His has only 22% exposed surface area in the crystal structure there was still room to fit a Phe (Eigenbrot et al., *J Mol Biol* 229(4):969-95 (1993)). The extra aromatic ring could pack against nearby residues and extend the hydrophobic core.

Ala occurred in only 6 ($V_L$49, $V_L$53, $V_L$55, $V_H$98, $V_H$99, $V_H$102) of the 19 residues that were randomized and it at a frequency of <6% for five of these residues, 14% for the other ($V_H$99). Four of these six residues were included in the alanine scan and all four of them were shown to decrease $K_D$ by 2-fold (Kelley et al., *Biochemistry* 31(24):5434-41 (1992)). The lack of alanine selection at these positions agreed with these results, provided that the HER2 binding selection under the conditions employed here was generally efficient in eliminating variants with >2-fold reductions in binding affinity. Analysis of Fab binding affinities of prevalent substitutions supported this (FIGS. 2 and 3) because all of the high-frequency frequency (>50%) variants showed binding affinities within 2-fold of wild-type. In contrast, a low-frequency (10%) substitution, Y100aF(VH), demonstrated about 5-fold weaker binding affinity than that of hu4D5-8 (FIG. 4).

The phage library selection was intended to select mutants with high affinity for antigen. Conservation of particular side chains could be the result of direct antigen contact, requirements for antibody structural stability or expression, or a combination of these effects. An example of a likely structure-stabilizing conservation was at G99($V_H$). $V_H$99 was a highly conserved residue in variable loop 3 of the heavy chain. This residue is position i+2 loop is a type II β-turn which is most commonly a Gly (Wilmot, C. M. & Thornton, J. M., *J Mol Biol* 203(1), 221-32 (1988)). Therefore, it seemed likely to be a structure-stabilizing residue.

Chemical Characteristics of Observed Substitutions

Aliphatic side chains were not specifically targeted in the libraries examined here. Perhaps not surprisingly, hydrophobic substitutions failed to dominate at any given site. However, there were a large number of hydrophobic residues that appeared at low levels in the mutated clones. Of these, the highest occurrence was only 23% for Leu substituted at R58 (VH).

Two polar side chains were well conserved: R50(VH) and R59(VH). However, H91(VL) and D98(VH) were more often substituted with a nonpolar aromatic residue, and T94(VL) was sometimes substituted with Trp. D98W(VH) was particularly interesting because it improved antigen binding as discussed below.

Conservation of chemical character occurred especially among aromatic and hydrophobic residues in the hu4D5-8 libraries. There are 6 residues ($V_H$100a, $V_H$56, $V_L$53, $V_H$33, $V_H$95, and $V_L$55) that favored an aromatic in 80% or more of the selected clones. Five positions ($V_L$49, $V_L$53, $V_L$91, $V_L$92, $V_H$100) selected aromatics 50% or more of the time. While there was often some bias towards one, in one case, $V_H$100, a Phe and a Trp occurred equally often (30% or 34%).

Three highly conserved residues were likely involved in a cation-π interaction. This interaction was between an Arg ($V_H$50), a Tyr ($V_H$33), and a Trp ($V_H$95) (Gallivan, J. P. & Dougherty, D. A., *Proc Natl Acad Sci USA* 96(17):9459-64 (1999)). When mutated in one library, Arg occurred at $V_H$50 in 93% of the clones. Trp $V_H$95 was selected in 59% of the clones and Tyr $V_H$33 in 61% of selected clones. Other amino acid substitutions at $V_H$95 and $V_H$33 were by other hydrophobic residues like Phe or Tyr ($V_H$95) and Trp ($V_H$33). These mutations were all likely to preserve the stabilizing chemistry with Arg $V_H$50. This result was supported by the fact that two of these residues, $V_H$50 and $V_H$95, drastically increased ΔΔG when mutated to alanine (Kelley, R. F. & O'Connell, M. P., *Biochemistry* 32(27):6828-35 (1993)).

Other aromatics were also conserved. On the surface of the hu4D5-8 binding site these surrounded a region of highly conserved residues (FIG. 7). Several of these mutations involved a set of putative π-π interactions. One example was at positions $V_L$53, $V_L$49 and $V_H$100. In hu4D5-8 these were a phenylalanine, a tyrosine, and a phenylalanine, respectively. The structure of hu4D5-8 illustrated that these residues were within 5 Å of each other and stacked the aromatic rings face to face or in the preferred T-shaped conformation typical of a π-π interaction (Burley, S. K. & Petsko, G. A., *Science* 229 (4708):23-8 (1985)). In the context of library 3 the outer phenylalanines were conserved while the Tyr in the middle preferred Phe in 28% of the selected clones. In a different library, that of library 5, all three residues were altered. At $V_L49$, 31% of the clones had a Trp while 55% had a Trp at $V_L53$ and 64% had either Trp or Phe at $V_L100$. The fact that these positions preferred aromatic amino acids in both of the libraries in which they were mutagenized suggested that conservation of the stabilizing π-π interaction on the surface of hu4D5-8 was important to antibody structure. They may have also contributed to antigen binding contacts.

Another π-π interaction appeared to occur between two tyrosines. ($V_L55$ and $V_H102$) located at the interface of the light and heavy chain. These tyrosines were in a T-shaped geometry and could be a source of stabilization. Surprisingly, this interaction was lost in the selected clones. Thirty-five percent of the clones replace $V_L55$ with Trp while $V_H102$ had a 19% occurrence of valine. Almost any other amino acid could occur at $V_H102$, but valine was slightly preferred.

Non-Additive Effects on Binding Free Energy

The hu4D5-8 phage libraries distributed 19 surface residues among 5 libraries. Several residues were present in more than one library to allow those in proximity to covary. Of the residues represented in duplicate libraries, some differences were observed based on context as noted above. However, based on a statistical analysis of covariation, there were no significant pair-wise correlations of substitutions at any of these positions, although a much larger number of sequences might make these correlations more apparent.

While most of the Fab mutants had slight negative effects on $K_D$, the combination of all tested point mutations in the multiple mutant M.7 still gave an improved binding affinity. Several single point mutations were clearly not additive in hu4D5-8 as mutations such as Y100aF($V_H$) and Y92W($V_L$) that adversely affected binding and/or folding stability were "rescued" by combinations with other mutations to a greater extent than would be predicted by additivity principles (Wells, J. A., *Biochemistry* 29(37), 8509-17 (1990)).

EXAMPLE 3

Hu4D5-8 Variant Fab Constructs

The assays discussed in Example 2 above demonstrated qualitatively that all tested clones retained high affinity (nanomolar to sub-nanomolar) binding affinity to antigen. In addition to those assays, the binding affinity of soluble Fab fragments was also tested.

Selection of Clones for Fab Binding Experiments

Eight clones using point mutations in the context of soluble Fab fragments, representing high frequency of occurrence of non-wild-type residues and a range of variability scores, were selected and tested to determine how selected substitutions affected HER2 binding as compared with the hu4D5-8 Fab.

Although siblings data were not used in analyzing the variety of mutations at individual sites, these data were considered in designing variants for binding experiments. It was reasoned that if a single clone was present in multiple copies after several rounds of selection it could potentially be due to improvements in binding, stability or expression. Three of the most abundant siblings were chosen: a triple mutant, called M.3 (N30($V_L$)S+H91($V_L$)F+Y92($V_L$)W) and the single mutants T94($V_L$)S and Y100a($V_H$)F. These clones represented roughly 20% of the total number of sequenced clones. All individual mutations were also combined into one multiple-mutant clone, M.7, (N30($V_L$)S+H91($V_L$)F+Y92($V_L$)W+T94($V_L$)S+D98($V_H$)W+Y100a($V_H$)F+Y102($V_H$)V).

Fab Constructs and Purification

Mutations were introduced with QuikChange® mutagenesis (Stratagene, La Jolla, Calif.) to Fab-expression plasmids pAK19 described previously (Carter et al., *Proc Natl Acad Sci USA* 89(10):4285-9 (1992b)). Hu4D5-8 Fab mutants were overexpressed by secretion in *E.coli* (Carter et al., *Biotechnology (N Y)* 10(2):163-7 (1992a)) and purified using a protein-G affinity column (Kelley et al., *Biochemistry* 31(24): 5434-41 (1992)). The concentration of each mutant was determined spectrophotometrically as well as by quantitative amino acid analysis; the two methods agreed within 5-12%.

Surface Plasmon Resonance (SPR) Binding Affinity Measurements

Surface plasmon resonance (SPR) was used to measure the binding kinetics of overexpressed Fabs to immobilized HER2-ECD receptor. A BIAcore-2000 or BIAcore-3000 real-time kinetic interaction analysis system (Biacore Inc., Piscataway, N.J.) was used to determine association ($k_{on}$) and dissociation ($k_{off}$) constants (Karlsson et al., *J Immunol Methods* 145(1-2):229-40 (1991)) of the hu4D5-8 Fab mutants. A B1 biosensor chip (Biacore, Inc.) was activated according to the manufacturer's instructions and immobilized with 86 to 500 RU's (response units) of HER2-ECD in 10 mM sodium acetate, pH 4.8. Unreacted groups were blocked with 1M ethanolamine. The kinetics of hu4D5-8 mutants binding to immobilized HER2-ECD were measured with 2-fold serial dilutions beginning with 100 nM Fab in running buffer (PBS, 0.05% Tween, 0.01% sodium azide) at a flow rate of 20 µl/min. Binding measurements were recorded at 19° C., 25° C., 31° C., and 37° C. at 4 different densities of immobilized HER2-ECD. Data were fit to a 1:1 Langmuir binding model using BIAcore evaluation software version 3 which calculated association ($k_{on}$) and dissociation ($k_{off}$) rates. An equilibrium constant, $K_D$, was calculated from $k_{off}/k_{on}$. Free energy differences, as compared with wild-type hu4D5-8 were calculated as described (Wells, J. A., *Biochemistry* 29(37), 8509-17 (1990)): $\Delta\Delta G = -RT \ln(K_D^{(mutant)}/K_D^{(wild-type)})$.

Antigen Binding Affinities of Fab Variants

Kinetics data for mutant Fabs binding to HER2-ECD at physiological temperature (37° C.) is shown in FIG. 4. The Fab mutants generally had very similar association and dissociation rate constants, $k_{on}$ and $k_{off}$. As a result, most of the mutants had $K_D$'S similar to hu4D5-8 Fab. One mutant, Y100a($V_H$)F, had a 4-fold negative affect on $K_D$. Two mutants had improved $K_D$'S, the multi-mutant M.7, (N30($V_L$)S+H91($V_L$)F+Y92($V_L$)W+T94($V_L$)S+D98($V_H$)W+Y100a($V_H$)F+Y102($V_H$)V), by 1.5 fold and single mutant D98($V_H$)W by about 3-fold at 37° C. (FIG. 4).

Figure 6:
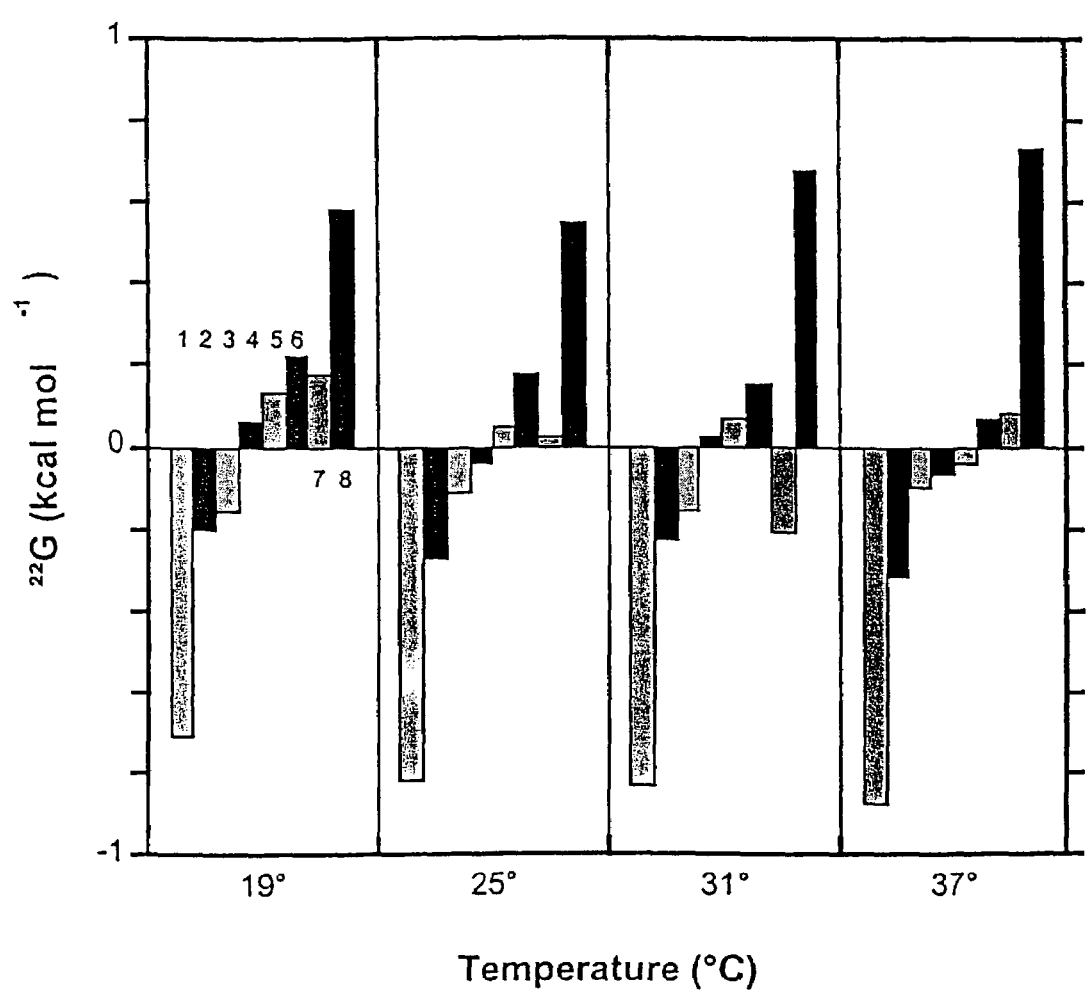
FIG. 6 shows the binding affinities of Fab variants to HER2-ECD. Mutants are compared to wild-type at each temperature indicated. Over this temperature range WT becomes slightly weaker ($\Delta\Delta G$=0.20) at higher temperatures. Differences in binding energies ($\Delta\Delta G$) as compared with hu4D5-8 were calculated for each mutant using $K_D$ values as shown in FIG. 4: ($\Delta\Delta G = \Delta G(WT) - \Delta G(mutant) = -RT \ln(K_D^{(mutant)}/K_D^{(wild-type)})$. The order of mutants represented is the same for each temperature panel: (1) Y100a($V_H$)F; (2) T94($V_L$)S; (3) Y102($V_L$)V; (4) N30($V_L$)S; (5) H91($V_L$)F; (6) N30($V_L$) S+H91($V_L$)F+Y92($V_L$)W; (7) the multiple mutant N30($V_L$) S+H91($V_L$)F+Y92($V_L$)W+T94($V_L$)S+D98($V_H$)W+Y100a ($V_H$)F+Y102($V_H$)V; and (8) D98($V_H$)W.

Over a temperature range of 19°-37° C., all of the variants tested showed binding energies well within 1.0 kcal/mol of that for binding of the wild-type hu4D5-8 to HER2 (FIG. 6). Over the same range, hu4D5-8 affinity was essentially constant, with $K_D$ ranging from 0.13 to 0.33 nM.

Binding constants for mutant Y92($V_L$)W were not reported because it expressed 10-fold more poorly than any of the other Fabs and showed poor binding to HER2. While it was selected by phage, these results indicate that Y92($V_L$)W was unable to function in the wild-type hu4D5-8 background. Interestingly, this mutation was "rescued" in the context of either of the multiple mutants, M.3 or M.7. Fusion to the g3 protein may assist in folding, as observed for certain phage displayed mutants of IGF-1 which were poorly behaved as soluble proteins (Dubaquie, Y. & Lowman, H. B., *Biochemistry* 38(20):6386-96 (1999)).

Identification of an Affinity-Improved Variant

The binding affinity of hu4D5-8 Fab has been reported to be in the sub-nanomolar range (Kelley, R. F. & O'Connell, M. P., *Biochemistry* 32(27):6828-35 (1993)). A single mutant, D98($V_H$)W, was selected as having a 3-fold improvement over WT. D98($V_H$) is located at the tip of variable loop 3 of the heavy chain and is the most protruding residues on the surface of the antibody (Eigenbrot et al., *J Mol Biol* 229(4):969-95 (1993)). Furthermore, it is adjacent to W95($V_H$), one of the four strong hits in the alanine scan. D98($V_H$) is the most variable position of all randomized 19 residues. Trp does not dominate the selected pool, but is the most frequent substitution selected. The location Trp $V_H$98 on the surface next to the putative binding site suggests this could be a site of sequence plasticity that directly contacts antigen.

EXAMPLE 4

Stringent Off-rate Binding Selection Using 4D5 Fab-phage Libraries

To search for additional high-affinity variants of humanized 4D5, the five libraries of 4D5 variants described in the previous Examples (see, also Gerstner et al., *J. Mol. Biol.* 321, 851-862 (2002)) were used for binding selections with immobilized HER2 as the binding target. Additional libraries were designed and constructed based upon the results of selections using the initial libraries. In particular, libraries 6 and 7 were designed to target a combination of residues identified in the initial libraries with restricted diversity using selected degenerate codons, and to include diversity at positions proximal to those identified earlier. Table 2 summarizes the diversity engineered into these libraries.

TABLE 2

Design of 4D5 libraries 5 and 6.

| Library | Chain | Position | Codon | Residues Encoded |
|---|---|---|---|---|
| Library-6 | VL | 30 | ARC | N, S |
| | VL | 49 | KKS | F, L, W, V(2), C, G(2) |
| | VL | 53 | TKS | W, F, L, C |
| | VL | 55 | TDS | W, L, F, C, Q*, Y |
| | VL | 91 | YWC | F, H, L, Y |
| | VL | 92 | TDS | W, L, F, C, Q*, Y |
| | VL | 94 | WCC | S, T |
| | VH | 100 | WKS | F, L, C, W, I, M |
| | VH | 102 | STC | L, V |
| Library-7 | VL | 27 | NNK | (all) |
| | VL | 28 | NNK | (all) |
| | VL | 30 | ARC | N, S |
| | VL | 31 | NNK | (all) |
| | VL | 32 | NNK | (all) |
| | VL | 66 | NNK | (all) |
| | VL | 91 | YWC | F, H, L, Y |
| | VL | 92 | TDS | W, L, F, C, Q*, Y |

In the foregoing Table 2 positions are shown according to the numbering system of Kabat (Kabat et al., *Sequences of Proteins of Immunological Interest*, 5$^{th}$ Edition, National Institutes of Health, Bethesda, Md. (1991)). Degenerate codons are shown using IUPAC code (R=A/G, Y=C/T, D=A/G/T, K=G/T, S=G/C, W=G/T, N=A/G/C/T).

In this series of binding-selection experiments, 4D5-phage libraries were propagated and subjected to sorting essentially as described (Lowman, *Methods Mol. Biol.* 87, 249-264 (1998); Chen et al., *J. Mol. Biol.* 293, 865-881 (1999)). Briefly, immunosorbant plates (Nunc Maxisorp) were coated with 2 μg/mL HER2-ECD in PBS (phosphate buffered saline) and blocked with BSA (bovine serum albumin). Thereafter, phage were added at a concentration of about 1011 phage/mL in PBS containing BSA and Tween-20.

For stringent off-rate selections, phage binding was allowed to reach equilibrium over a period of 16 hours or longer, followed by washing with PBS/Tween-20, and dissociation in wash buffer containing 0.01% sodium azide (with or without rhuMAb 4D5 antibody) for progressively longer periods of time (Table 3). Phage were eluted with a brief (10 min.) incubation with 100 mM HCl, neutralized, and propagated overnight in XL1-Blue cells (Stratagene) as described (Lowman, 1998, supra).

TABLE 3

Conditions for off-rate binding selections

| Round | Binding time | Washes | Dissoc. Time | Dissoc. Buffer |
|---|---|---|---|---|
| 1 | 48 h | 10 x | — | — |
| 2 | 16 h | 20 x | 3 h | Wash buffer |
| 3 | 16 h | 10 x daily | 48 h | Wash buffer + 100 nM 4d5 |
| 4 | 16 h | 10 x daily | 120 h | Wash buffer + 100 nM 4d5 |

Binding enrichments were measured by comparison of recovered phage titers from HER2 versus BSA wells. The results over increasingly stringent rounds of binding selection showed enrichment of HER2-ECD binding phage over background binding for each library except library 4 (data not shown).

Phage clones were isolated after four rounds of binding selection for sequencing and further characterization. The sequences of these clones are shown in Table 4, in comparison with the wild-type (rhuMAb 4D5) residue at each position. A statistical test of significance (Lowman & Wells, J. Mol. Biol. 234, 564-578 (1993)) was applied to define favored substitutions at each position where non-wild-type residues were commonly observed (Table 4). Briefly, the observed frequency (Pobs) of each amino acid is compared to the expected (random) frequency determined from the number of codons that can encode that amino acid (Pexp), using a particular codon degeneracy. The significance score, S, is calculated as S=(Pobs−Pexp)/σ, where σ is the standard deviation of the theoretical random distribution (Lowman & Wells, 1993, supra).

TABLE 4

Sequences of 4d5-phage isolates after four rounds of off-rate binding selection using immobilized HER2-ECD.

| | Library 1 | | | | | |
|---|---|---|---|---|---|---|
| | VL | | | VH | | |
| Position: | 94 | 33 | 50 | 56 | 58 | 95 |
| WT | T | Y | R | Y | R | W |
| 4d5.26 | T | Y | R | A | R | W |

TABLE 4-continued

Sequences of 4d5-phage isolates after four rounds of off-rate binding selection using immobilized HER2-ECD.

| | | | | | | |
|---|---|---|---|---|---|---|
| 4d5.29 | T | Y | R | Y | R | Y |
| 4d5.32 | T | Y | R | Y | R | Y |
| 4d5.34 | T | Y | R | Y | R | Y |
| 4d5.37 | T | | | | | Y |
| 4d5.39 | T | | | | | Y |
| 4d5.41 | T | W | R | Y | R | F |
| 4d5.44 | T | | | | | F |
| 4d5.45 | T | Y | R | A | R | W |
| 4d5.35 | T | W | R | W | I | Y |
| 4d5.36 | T | W | R | W | I | Y |
| 4d5.27 | T | Y | R | Y | R | F |
| 4d5.33 | T | Y | R | Y | R | W |
| 4d5.30 | T | Y | R | Y | R | Y |
| 4d5.43 | T | | | | | Y |
| 4d5.38 | T | Y | R | Y | R | Y |
| 4d5.42 | T | F | R | Y | R | W |
| Consensus changes: | | | | | | Y |
| Significance score: | | | | | | 13 |

Library 2

| | VL | | | VH | | | |
|---|---|---|---|---|---|---|---|
| Position: | 30 | 91 | 92 | 50 | 95 | 99 | 100a |
| WT | N | H | Y | R | W | G | Y |
| 4d5.1 | S | F | W | | | | |
| 4d5.10 | S | F | W | R | W | G | Y |
| 4d5.12 | S | F | W | R | W | G | Y |
| 4d5.7 | S | F | W | | | | |
| 4d5.3 | S | Y | W | | | | |
| 4d5.8 | S | F | W | R | W | G | Y |
| 4d5.11 | S | | W | R | W | G | Y |
| 4d5.9 | S | F | F | R | W | G | Y |
| 4d5.2 | S | F | G | R | W | G | Y |
| 4d5.4 | S | Y | G | R | W | G | Y |
| 4d5.5 | S | I | W | R | W | G | Y |
| 4d5.6 | S | F | W | R | W | G | Y |
| Consensus changes: | S | F | W | | | | |
| Significance score: | 11 | 13 | 14 | | | | |

Library 3

| | VL | | | VH | | | |
|---|---|---|---|---|---|---|---|
| Position: | 49 | 53 | 91 | 98 | 99 | 100 | 100a |
| WT | Y | F | H | D | G | F | Y |
| 4d5.15 | W | V | Y | H | G | M | Y |
| 4d5.22 | W | F | Y | A | G | F | N |
| 4d5.16 | L | F | H | R | S | Y | Y |
| 4d5.24 | F | F | Y | A | S | L | F |
| 4d5.21 | W | V | F | R | G | L | Y |
| 4d5.23 | S | W | F | S | G | F | Y |
| 4d5.18 | K | F | Y | T | G | A | Y |
| 4d5.19 | Y | F | F | K | G | F | Y |
| 4d5.13 | V | W | Y | | | | |
| 4d5.14 | V | F | F | | | | |
| 4d5.17 | F | W | Y | L | G | H | Y |
| 4d5.20 | L | V | | H | L | Y | Y |
| 4d5.31 | L | L | T** | | | | |
| 4d5.28 | W | W | W | | | V | |
| Consensus changes: | W | W | Y/F | basic | | | |
| Significance score: | 5.5 | 5.5 | 8.9/5.7 | 3.0 | | | |

Library 5

| | VL | | | VH | |
|---|---|---|---|---|---|
| Position: | 49 | 53 | 55 | 100 | 102 |
| WT | Y | F | Y | F | Y |
| 4d5.50 | D | W | W | P | K |
| 4d5.51 | D | W | W | P | L |
| 4d5.52 | D | W | W | P | L |
| 4d5.54 | V | T | W | P | W |
| 4d5.53 | Y | F | W | | |

TABLE 4-continued

Sequences of 4d5-phage isolates after four rounds of off-rate binding selection using immobilized HER2-ECD.

| | | | | | |
|---|---|---|---|---|---|
| 4d5.59 | F | H | W | W | M |
| 4d5.57 | V | V | W | W | L |
| 4d5.60 | A | V | L | H | L |
| 4d5.49 | W | R | W | | |
| 4d5.55 | W | Q | F | F | W |
| 4d5.56 | V | W | L | P | H |
| 4d5.58 | W | T | Y | F | Y |
| 4d5.89 | D | W | W | | |
| 4d5.92 | D | W | W | P | K |
| 4d5.93 | D | W | W | P | L |
| 4d5.94 | D | W | W | | |
| 4d5.77 | Y | F | W | P | K |
| 4d5.86 | F | H | W | | |
| 4d5.85 | E | W | W | | |
| 4d5.96 | R | W | V | | |
| 4d5.87 | T | K | W | | |
| 4d5.91 | R | A | W | | |
| 4d5.88 | T | R | V | | |
| 4d5.90 | V | K | S | M | A |
| 4d5.95 | S | V | W | | |
| Consensus changes: | D | W | W | P | |
| Significance score: | 7.1 | 11 | 20 | 7.9 | |

Library 6

| | VL | | | | | | | VH | |
|---|---|---|---|---|---|---|---|---|---|
| (restricted) Position: | 30 | 49 | 53 | 55 | 91 | 92 | 94 | 100 | 102 |
| WT | N | Y | F | Y | H | Y | T | F | Y |
| 4d5.63 | N | V | W | W | H | Y | T | | |
| 4d5.64 | | | | | | | | L | S |
| 4d5.65 | N | V | W | W | H | Y | T | L | S |
| 4d5.66 | N | V | W | W | H | Y | T | | |
| 4d5.68 | N | V | W | W | H | Y | T | | |
| 4d5.70 | N | V | W | W | H | Y | T | L | S |
| 4d5.61 | N | F | K | W | H | Y | T | L | T |
| 4d5.71 | N | V | W | W | H | Y | T | | |
| 4d5.67 | N | V | R | A | H | Y | T | M | G |
| 4d5.69 | N | V | R | A | H | Y | T | M | G |
| 4d5.62 | N | W | L | P | H | Y | T | M | |
| 4d5.72 | N | L | M | G | H | Y | T | R | L |
| Consensus changes: | | V | W | W | | | | | |
| Significance score: | | 6 | 2.3 | 4.2 | | | | | |

Library 7

| | VL | | | | | | | VH | |
|---|---|---|---|---|---|---|---|---|---|
| (restricted) Position: | 27 | 28 | 30 | 31 | 32 | 66 | 91 | 92 | 100 102 |
| WT | Q | D | N | T | A | R | H | Y | F Y |
| 4d5.73 | S | Q* | S | S | G | R | H | W | |
| 4d5.76 | S | Q* | S | G | G | R | H | W | P A |
| 4d5.75 | R | Q* | N | T | A | R | F | F | |
| 4d5.83 | A | Q* | S | A | G | R | Y | W | P V |
| 4d5.79 | Q* | G | S | S | G | A | H | W | |
| 4d5.80 | Q* | G | S | S | A | N | H | W | P K |
| 4d5.78 | Q | R | N | S | A | R | H | F | |
| 4d5.81 | Q* | G | S | S | A | M | H | F | P L |
| 4d5.74 | N | P | S | Q | A | T | H | W | |
| 4d5.84 | S Q* | S | K | A | S | Y | L | P | L |
| 4d5.82 | F | | N | A | C | V | H | Q* | P L |
| Consensus changes: | | Q | | S | G | | | W | P |
| Significance score: | | 5.7 | 4.1 | 4.1 | | | | 3.4 | 5.5 |

No sequencable clones were recovered from round 4 of selections using Library 4. In the foregoing table Gln residues encoded by read-through of the amber stop codon (TAG) are indicated by Q*. A spontaneous mutation (VH Y102M) was identified at a site not targeted for mutagenesis in the original libraries (**). Consensus residues are shown for positions where non-wild-type residues occurred with significant frequency. The restricted codon selections used in libraries 6-7 are described in Table 2. In Library 3, "basic" residues refer to a combination of H, K, and R. Blanks indicate uncertain or undetermined sequence at the corresponding position.

The occurrence of non-wild-type residues may reflect improved binding affinity, stability, and/or expression level for variants containing those substitutions. However, in previous affinity maturation studies, significance scores >2 have often correlated with improvements in binding affinity (Lowman & Wells, 1993, supra). Therefore, based upon the sequence-significance scores from Table 4, substitutions that may improve the binding affinity of 4d5 for HER2 are listed in Table 5. These substitutions can be compared with the finding of Gerstner et al. (2002), supra. For example, in that work, using solution-phase capture of 4D5-phage, several of the substitutions identified here were also found. Some positions showed similar substitutions, for example, VL mutations F53W, Y55W, and Y92W, were commonly found in the previous experiments. However, substitutions not commonly found in the previous experiments include basic residues (R, K, H) substituting at VH position 98, and P substituting at VH position 100. These mutations may act individually, or in combination with other mutations to improve binding affinity of 4D5 for HER2.

TABLE 5

Summary of consensus residues by position from off-rate selections.

| Chain | Position | Preferred residue(s) |
|---|---|---|
| VL | D28 | Q |
| VL | N30 | S |
| VL | T31 | S |
| VL | A32 | G |
| VL | Y49 | W, D, V |
| VL | F53 | W |
| VL | Y55 | W |
| VL | H91 | Y, F |
| VL | Y92 | W |
| VH | W95 | Y |
| VH | D98 | R, K, H |
| VH | F100 | P |

EXAMPLE 5

Screening of Selected 4D5 Clones from Off-rate Selection

Selected representative clones were chosen for further characterization in competitive phage-ELISA assays (Lowman, 1998). Several variants appeared to have improved binding to HER2-ECD as compared with wild-type 4D5 Fab (Table 6). Because of the relatively high affinity of wild-type 4D5, this assay does not provide a reliable measure of affinity-matured versions of 4D5 (Gerstner et al., 2002); however, we have used the assay to rank clones for further analysis.

TABLE 6

Competitive phage-ELISA results for selected 4d5-phage.

| Clone | Relative $IC_{50}$ | s.d. |
|---|---|---|
| WT | -1- | — |
| 4d5.2 | 0.15 | 0.11 |
| 4d5.4 | 0.21 | 0.15 |
| 4d5.17 | 0.09 | 0.07 |
| 4d5.21 | 1.98 | 1.41 |
| 4d5.22 | 0.06 | 0.04 |
| 4d5.28 | 0.10 | 0.07 |
| 4d5.31 | 0.18 | 1.06 |
| 4d5.35 | 0.35 | 1.04 |
| 4d5.44 | 0.40 | 0.82 |
| 4d5.50 | 1.49 | 0.85 |
| 4d5.51 | 1.47 | 0.28 |
| 4d5.55 | 1.16 | 0.04 |
| 4d5.57 | 1.20 | 0.85 |
| 4d5.64 | 0.40 | 0.28 |
| 4d5.67 | 0.05 | 0.04 |
| 4d5.80 | 1.93 | 1.37 |
| 4d5.81 | 1.26 | 0.89 |
| 4d5.83 | 0.08 | 0.06 |
| 4d5.84 | 0.21 | 0.14 |
| 4d5.92 | 2.08 | 0.67 |
| D98W.1 | 2.76 | 1.13 |
| D98W.2 | 3.77 | 0.95 |

The relative IC50 reported is calculated as $IC_{50}$(wild-type)/$IC_{50}$(variant); values >1 reflect higher apparent affinities than wild-type. Errors are reported as standard deviations (s.d.). For comparison, values for two independent clones of a previously reported variant, D98W (VH) are also shown.

Based on the results of phage-ELISA assays, several variants were predicted to have improved binding affinity to HER2: 4d5.21, 4d5.50, 4d5.51, 4d5.55, 4d5.57, 4d5.80, 4d5.81, and 4d5.92. The point mutations identified among all these clones are summarized in Table 7. These mutations are therefore implicated as acting separately or synergistically to improve binding affinity of 4d5 to HER2.

TABLE 7

Summary of point mutations by position found among highest affinity variants identified by phage-ELISA screening.

| Chain | Position | Preferred residue(s) |
|---|---|---|
| VL | D28 | G |
| VL | N30 | S |
| VL | T31 | S |
| VL | Y49 | W*, D*, V |
| VL | F53 | V*, W*, Q |
| VL | R66 | N, M |
| VL | H91 | F*, W* |
| VL | Y92 | W, F |
| VH | D98 | R*, W |
| VH | F100 | P*, L*, W |
| VH | Y102 | W, L, K* |

Mutations occurring in the two highest apparent-affinity variants, 4d5.21 and 4d5.92, are indicated (*).

EXAMPLE 6

Affinity Measurements of Selected 4D5 Clones Fromo Off-rate Selection

To determine equilibrium binding affinities (Kd) of Fab variants, soluble Fab fragments produced in *E. coli* and tested in a BIAcore binding assay (Gerstner et al, 2002) using immobilized HER2-ECD at 37° C. Fab concentrations were determined by quantitative amino acid analysis. The results of kinetic measurements are summarized in Table 8.

TABLE 8

Binding kinetics and affinities of selected 4d5 Fab variants using a surface-plasmon resonance assay (BIAcore).

| Variant | $k_{on}$ (/10$^6$/M/s) | $k_{off}$ (10$^4$/s) | $K_d$ (pM) | s.d. | n | Relative Affinity |
|---|---|---|---|---|---|---|
| 4d5.51 | 1.32 | 0.18 | 14 | 8 | 2 | 7.6 |
| 4D5.80 | 1.49 | 0.23 | 16 | n/a | 1 | 6.7 |
| D98W | 2.99 | 0.80 | 27 | 15 | 12 | 3.9 |
| 4d5.50 | 1.94 | 0.81 | 42 | 25 | 3 | 2.5 |
| 4d5.21 | 3.57 | 2.60 | 73 | 28 | 9 | 1.4 |
| WT | 1.90 | 2.01 | 105 | 29 | 12 | 1.0 |
| 4D5.55 | 1.56 | 4.40 | 281 | 72 | 10 | 0.4 |

In the foregoing Table 8 equilibrium dissociation affinities (Kd) are calculated as koff/kon, for n measurements. Errors are shown as standard deviations (s.d.). The relative affinity is calculated as Kd(WT)/Kd(variant); values >1 indicate higher apparent affinity for HER2-ECD.

The results of these experiments indicate that Fabs corresponding to phage clones 4d5.51, 4d5.80, and 4d5.50, as well as the previously described point mutant D98W (VH) each have >2-fold improved binding to HER2-ECD as compared with WT. For comparison, the substitutions found in each of these variants are summarized in Table 9. On the other hand, 4D5.21 and 4D5.55 have little improvement, or are slightly weaker in binding.

Comparison of relative on-rates and off-rates indicates that while D98W, identified by solution-phase binding selections (Gerstner et al, 2002) was improved in both kon and koff, the best variants identified by stringent off-rate selections using immobilized 4d5 consistently had slower koff, with slower kon as compared with WT.

TABLE 9

Point mutation in affinity-improved 4d5 variants identified by kinetics analysis. Residues differing from WT are shown in bold; residues identical to WT are shown (-).

| Variant Position: | VL 27 | VL 28 | VL 30 | VL 31 | VL 32 | VL 49 | VL 53 | VL 55 | VL 66 | VL 91 | VL 92 | VH 98 | VH 100 | VH 102 |
|---|---|---|---|---|---|---|---|---|---|---|---|---|---|---|
| WT | Q | D | N | T | A | Y | F | Y | R | H | Y | D | F | Y |
| 4d5.50 | - | - | - | - | - | D | W | W | - | - | - | - | P | K |
| 4d5.51 | - | - | - | - | - | D | W | W | - | - | - | - | P | L |
| 4d5.80 | - | G | S | S | - | - | - | - | N | - | W | - | P | K |
| D98W | - | - | - | - | - | - | - | - | - | - | - | W | - | - |

EXAMPLE 7

4D5 Variants Produced by Combinations of Selected Mutations

Because mutations could act individually or in combination with other mutations found in the same 4d5-phage selectant, we were interested in testing combinations of mutations from the highest affinity variants, including the previously described D98W (VH). A set of variants were designed to test the contributions of "DWW" (i.e., VL mutations D49D/F53W/Y55W) alone, as well as "DWW" and "PL" or "PK" (i.e., VH mutations F100P/Y102K or F100P/Y102L) in combination with the VH mutations D98W (Table 10).

TABLE 10

Combination variants of 4d5.

| Variant Position: | VL 27 | VL 28 | VL 30 | VL 31 | VL 32 | VL 49 | VL 53 | VL 55 | VL 66 | VL 91 | VL 92 | VH 98 | VH 100 | VH 102 |
|---|---|---|---|---|---|---|---|---|---|---|---|---|---|---|
| WT | Q | D | N | T | A | Y | F | Y | R | H | Y | D | F | Y |
| 4d5-D98W-PK | - | - | - | - | - | - | - | - | - | - | - | W | P | K |
| 4d5-D98W-PL | - | - | - | - | - | - | - | - | - | - | - | W | P | L |

TABLE 10-continued

Combination variants of 4d5.

| Variant Position: | VL 27 | VL 28 | VL 30 | VL 31 | VL 32 | VL 49 | VL 53 | VL 55 | VL 66 | VL 91 | VL 92 | VH 98 | VH 100 | VH 102 |
|---|---|---|---|---|---|---|---|---|---|---|---|---|---|---|
| 4d5-DWW | – | – | – | – | – | D | W | W | – | – | – | – | – | – |
| 4d5-D98W-DWW | – | – | – | – | – | D | W | W | – | – | – | W | – | – |

Variant Fabs were produced by site-directed mutagenesis, expressed in *E. coli*, and assayed by BIAcore binding at 37° C. In these assays, association and dissociation constants were measured as previously described (Gerstner et al., 2002), except that the dissociation phase of each experiment was extended to 30 min. to permit more accurate measurement of the very slow koff rates observed, Results are shown in Table 11.

TABLE 11

Binding affinities from kinetics analysis (BIAcore) of 4d5 variants combining mutations from selected 4d5-phage variants.

| Variant | $k_{on}$ (/10$^6$/M/s) | $k_{off}$ (10$^{-4}$/s) | $K_d$ (nM) | s.d. | n | Relative Affinity |
|---|---|---|---|---|---|---|
| WT | 0.69 | 2.19 | 317 | 87 | 6 | 1.00 |
| D98W | 1.26 | 0.95 | 75 | 27 | 6 | 4.23 |
| 4d5.50 | 0.87 | 0.87 | 111 | 50 | 3 | 2.86 |
| 4d5.51 | 0.67 | 0.53 | 69 | 17 | 3 | 4.62 |
| 4d5.80 | N.D. | N.D. | N.D. | N.D. | N.D. | N.D. |
| 4d5-D98W-PK | 0.44 | 5.04 | 1146 | 109 | 3 | 0.28 |
| 4d5-D98W-PL | 0.50 | 4.29 | 856 | 141 | 3 | 0.37 |
| 4d5-DWW | N.D. | N.D. | N.D. | N.D. | N.D. | N.D. |
| 4d5-PK | N.D. | N.D. | N.D. | N.D. | N.D. | N.D. |
| 4d5-D98W-DWW | N.D. | N.D. | N.D. | N.D. | N.D. | N.D. |

In the foregoing table, Kon and koff were fit separately using the BIAcore BIAevaluation software. Equilibrium dissociation affinities Kd) are calculated as koff/kon, for n measurements. Errors are shown as standard deviations (s.d.). The relative affinity is calculated as Kd(WT)/Kd(variant); values >1 indicate higher apparent affinity for HER2-ECD, N.D.=not determined.

The results of these long-dissociation assays confirmed that variants D98W, 4d5.50, and 4d5.51 have improved binding affinity to HER2 as compared with wild-type. However, combinations of D98W with 100P/Y102K or F100P/Y102L did not produce additive improvements in these experiments.

All references cited herein and throughout the specification are hereby expressly incorporated by reference.

Deposit of Biological Material

The following hybridoma cell lines have been deposited with the American Type Culture Collection, 10801 University Boulevard, Manassas, Va. 20110-2209, USA (ATCC):

| Antibody Designation | ATCC No. | Deposit Date |
|---|---|---|
| 4D5 | ATCC CRL 10463 | May 24, 1990 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample. (Rule 28(4) EPC).

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein. The examples of the products of the present invention and representative processes for their isolation, use, and manufacture should not be construed to limit the invention.

What is claimed is:

1. An isolated antibody that is capable of binding to the extracellular domain of HER2, which comprises an antibody light chain variable domain of SEQ ID NO: 1, and an antibody heavy chain variable domain of SEQ ID NO: 2, wherein the light chain variable domain of SEQ ID NO: 1 comprises an amino acid substitution selected from the group consisting of N30($V_L$)S; T31($V_L$)S; Y49($V_L$)D, and Y49($V_L$)W numbered according to the Kabat numbering system, and the heavy chain variable domain of SEQ ID NO: 2 comprises an amino acid substitution selected from the group consisting of D98($V_H$)W, F100($V_H$)P; Y102($V_H$)K; and Y102($V_H$)L, numbered according to the Kabat numbering system.

2. The antibody of claim 1 wherein the amino acid substitution in the light chain variable domain is Y49($V_L$)D.

3. The antibody of claim 1, wherein the amino acid substitution in the light chain variable domain is N30($V_L$)S.

4. An isolated antibody that is capable of binding to the extracellular domain of HER2, which comprises an antibody light chain variable domain of SEQ ID NO: 1, wherein N30 ($V_L$) is substituted with S, H91($V_L$) is substituted with F, and Y92($V_L$) is substituted with W, numbered according to the Kabat numbering system, and an antibody heavy chain variable domain of SEQ ID NO: 2, comprising an amino acid substitution selected from the group consisting of substitutions D98($V_H$)R, F100($V_H$)P and Y102($V_H$)K, numbered according to the Kabat numbering.

5. The antibody of claim 1, which is a humanized antibody.

6. The antibody of claim 1, which is a antibody fragment selected from the group consisting of Fv, Fab, Fab' and F(ab')$_2$ fragments.

7. The antibody of claim 1 wherein the amino acid substitution in the heavy chain variable domain is D98($V_H$)W.

8. The antibody of claim 1 wherein the amino acid substitution in the heavy chain variable domain is F100($V_H$)P or Y102($V_H$)K.

9. The antibody of claim 1 wherein the amino acid substitution in the heavy chain variable domain is F100($V_H$)P or Y102($V_H$)L.

10. An isolated antibody that is capable of binding to the extracellular domain of HER2, which comprises an antibody light chain variable domain of SEQ ID NO: 1, and an antibody heavy chain variable domain of SEQ ID NO: 2, wherein said light chain variable domain comprises an amino acid substitution selected from the group consisting of Y49($V_L$)D, F53 ($V_L$)W, and Y55($V_L$)W, numbered according to the Kabat numbering system.

11. An isolated antibody that is capable of binding to the extracellular domain of HER2, which comprises an antibody light chain variable domain of SEQ ID NO: 1 and an antibody heavy chain variable domain of SEQ ID NO: 2, wherein in said light chain variable region N30($V_L$) is substituted with S, H91($V_L$) is substituted with F, and Y92($V_L$) is substituted with W.

12. The antibody of claim 10 or 11, which is a humanized antibody.

13. The antibody of claim 10 or 11, which is an antibody fragment selected from the group consisting of Fv, Fab, Fab' and F(ab')$_2$ fragments.

14. An isolated antibody that is capable of binding to the extracellular domain of HER2, which comprises an antibody light chain variable domain of SEQ ID NO: 1 and an antibody heavy chain variabic domain of SEQ ID NO: 2, wherein said heavy chain variable domain comprises amino acid substitutions F100($V_H$)P and Y102($V_H$)K, numbered according to the Kabat numbering.

15. The antibody of claim 14, which is a humanized antibody.

16. The antibody of claim 14, which is an antibody fragment selected from the group consisting of Fv, Fab, Fab' and F(ab')$_2$ fragments.

17. An antibody that is capable of binding to the extracellular domain of HER2, which comprises an antibody light chain variable domain of SEQ ID NO: 1 and an antibody heavy chain variable domain of SEQ ID NO: 2, wherein in the light chain variable domain N30($V_L$) is substituted with S, H91($V_L$) is substituted with F, Y92($V_L$) is substituted with W, T94($V_L$) is substituted with S, and in the heavy chain variable domain D98($V_H$) is substituted with W, Y100a($V_H$) is substituted with F, and Y102($V_H$) is substituted with V, numbered according to the Kabat numbering system.

18. An isolated antibody that is capable of binding to the extracellular domain of HER2, which comprises comprising an antibody light chain variable domain of SEQ ID NO: 1 and an antibody heavy chain variable domain of SEQ ID NO: 2 with the following substitutions: Y49($V_L$)D, F53($V_L$)W, Y55 ($V_L$)W, F100($V_H$)P, and Y102($V_H$)L.

19. The antibody of claim 18 wherein the heavy chain variable domain of SEQ ID NO: 2 further comprises the substitution D98($V_H$)W.

20. An isolated antibody that is capable of binding to the extracellular domain of HER2, which comprises an antibody light chain variable domain of SEQ ID NO: 1 and an antibody heavy chain variable domain of SEQ ID NO: 2 with the following substitutions: Y49($V_L$)D, F53($V_L$)W, Y55($V_L$)W, F100($V_H$)P, and Y102($V_H$)K.

21. The antibody of claim 20 wherein the the heavy chain variable domain of SEQ ID NO: 2 further comprises the substitution D98($V_H$)W.

22. The antibody of claim 18, 19, 20, or 21, wherein the binding affinity of the antibody for the HER2 extracellular domain is at least three-fold better than the binding affinity of humanized monoclonal antibody 4D5-8 for the HER2 extracellular domain.

23. The antibody of claim 18, 19, 20, or 21, which is a humanized antibody.

24. The antibody of claim 18, 19, 20, or 21, which is an antibody fragment selected from the group consisting of Fv, Fab, Fab' and F(ab')$_2$ fragments.

25. An isolated antibody that is capable of binding to the extracellular domain of HER2, which comprises an antibody light chain variable domain of SEQ ID NO: 1 and an antibody heavy chain variable domain of SEQ ID NO: 2, wherein N30($V_L$) is substituted with S, H91($V_L$) is substituted with F, and Y92($V_L$) is substituted with W, numbered according to the Kabat numbering system.

26. A humanized anti-HER2 antibody 4D5-8, comprising one or more amino acid substitutions selected from the group consisting of N30($V_L$)S, Y49($V_L$)W, F53($V_L$)W, H91($V_L$)F, Y92($V_L$)W, and D98($V_H$)W, numbered according to the Kabat numbering system.

27. A humanized anti-HER2 antibody 4D5-8, which comprises a combination of amino acid substitutions selected from the group consisting of (i) Y95($V_L$)W, F53($V_L$)V, H91($V_L$)F and D98($V_H$)R, F100($V_H$)L; (ii) Y49($V_L$)D, F53($V_L$)W, Y55($V_L$)W, F100($V_H$)P, Y102($V_H$)K; (iii) Y49($V_L$)D, F53($V_L$)W, Y55($V_L$)W, F100($V_H$)P, Y102($V_H$)L; (iv) Y49($V_L$)V, F53($V_L$)V, Y55($V_L$)W, F100($V_H$)W, Y102($V_H$)L; (v) Y49($V_L$)W, F53($V_L$)O, Y55($V_L$)F, Y102($V_H$)W; (vi) Y49($V_L$)D, F53($V_L$)W, Y55($V_L$)W, F100($V_H$)P, Y102($V_H$)K; (vii) D28($V_L$)G, N30($V_L$)S, T31($V_L$)S, R66($V_L$)N, Y92($V_L$)W, F100($V_H$)P, Y102($V_H$)K; and (viii) D28($V_L$)G, N30($V_L$)S, T31($V_L$)S, R66($V_L$)M, Y92($V_L$)F, F100($V_H$)P, Y102($V_H$)L.

28. An article of manufacture comprising a container, a composition contained therein, and a package insert or label indicating that the composition can be used to treat cancer characterized by the overexpression of HER2, wherein the composition comprises the antibody of claim 26 or 22.

29. The article of manufacture of claim 28, wherein the cancer is breast cancer.

30. An isolated antibody that is capable of binding to the extracellular domain of HER2, which comprises an antibody light chain variable domain of SEQ ID NO:1 and an antibody heavy chain variable domain of SEQ ID NO: 2 wherein the heavy chain variable domain comprises an amino acid substitution 98($V_H$)W.

* * * * *

SEQUENCE LISTING

<160> NUMBER OF SEQ ID NOS: 24

<210> SEQ ID NO 1
<211> LENGTH: 109
<212> TYPE: PRT
<213> ORGANISM: homo sapiens

<400> SEQUENCE: 1

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr
            100                 105

<210> SEQ ID NO 2
<211> LENGTH: 120
<212> TYPE: PRT
<213> ORGANISM: homo sapiens

<400> SEQUENCE: 2

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser
        115                 120

<210> SEQ ID NO 3
<211> LENGTH: 33
<212> TYPE: DNA
<213> ORGANISM: homo sapiens
<220> FEATURE:
<221> NAME/KEY: misc_feature
<222> LOCATION: 16, 17
<223> OTHER INFORMATION: N=A, G, T or C
<220> FEATURE:
<221> NAME/KEY: misc_feature
<222> LOCATION: 18
<223> OTHER INFORMATION: S=G or C

```
<400> SEQUENCE: 3
gccagtcagg atgtgnnsac tgctgtagcc tgg                                    33

<210> SEQ ID NO 4
<211> LENGTH: 38
<212> TYPE: DNA
<213> ORGANISM: homo sapiens
<220> FEATURE:
<221> NAME/KEY: misc_feature
<222> LOCATION: 18, 19, 21, 22
<223> OTHER INFORMATION: N=A,G,T, or C
<220> FEATURE:
<221> NAME/KEY: misc_feature
<222> LOCATION: 20, 23
<223> OTHER INFORMATION: S=G or C

<400> SEQUENCE: 4
cttattactg tcagcaanns nnsactactc ctcccacg                               38

<210> SEQ ID NO 5
<211> LENGTH: 36
<212> TYPE: DNA
<213> ORGANISM: homo sapiens
<220> FEATURE:
<221> NAME/KEY: misc_feature
<222> LOCATION: 17, 18
<223> OTHER INFORMATION: N=A,G,T, or C
<220> FEATURE:
<221> NAME/KEY: misc_feature
<222> LOCATION: 19
<223> OTHER INFORMATION: S=G or C

<400> SEQUENCE: 5
cctggaatgg gttgcannsa tttatcctac gaatgg                                 36

<210> SEQ ID NO 6
<211> LENGTH: 54
<212> TYPE: DNA
<213> ORGANISM: homo sapiens
<220> FEATURE:
<221> NAME/KEY: misc_feature
<222> LOCATION: 17, 18, 29, 30, 35, 36
<223> OTHER INFORMATION: N=A,G,T or C
<220> FEATURE:
<221> NAME/KEY: misc_feature
<222> LOCATION: 19, 31, 37
<223> OTHER INFORMATION: S=G or C

<400> SEQUENCE: 6
ctattattgt tctagannsg gaggggacnn sttcnnsgct atggactact gggg             54

<210> SEQ ID NO 7
<211> LENGTH: 45
<212> TYPE: DNA
<213> ORGANISM: homo sapiens
<220> FEATURE:
<221> NAME/KEY: misc_feature
<222> LOCATION: 16, 17, 28, 29
<223> OTHER INFORMATION: N=A,G,T, or C
<220> FEATURE:
<221> NAME/KEY: misc_feature
<222> LOCATION: 18, 30
<223> OTHER INFORMATION: S=G or C

<400> SEQUENCE: 7
ccgaaactac tgattnnstc ggcatccnns ctctactctg gagtc                       45

<210> SEQ ID NO 8
<211> LENGTH: 40
```

```
<212> TYPE: DNA
<213> ORGANISM: homo sapiens
<220> FEATURE:
<221> NAME/KEY: misc_feature
<222> LOCATION: 23, 24
<223> OTHER INFORMATION: N=A, G, T, or C
<220> FEATURE:
<221> NAME/KEY: misc_feature
<222> LOCATION: 25
<223> OTHER INFORMATION: S=G or C

<400> SEQUENCE: 8
cgcaacttat tactgtcagc aannstatac tactcctccc                              40

<210> SEQ ID NO 9
<211> LENGTH: 45
<212> TYPE: DNA
<213> ORGANISM: homo sapiens
<220> FEATURE:
<221> NAME/KEY: misc_feature
<222> LOCATION: 18, 19, 21, 22, 24, 25, 27, 28
<223> OTHER INFORMATION: N=A, G, T or C
<220> FEATURE:
<221> NAME/KEY: misc_feature
<222> LOCATION: 20, 23, 26, 29
<223> OTHER INFORMATION: S=G or C

<400> SEQUENCE: 9
gttctagatg gggagggnns nnsnnsnnsg ctatggacta ctggg                        45

<210> SEQ ID NO 10
<211> LENGTH: 35
<212> TYPE: DNA
<213> ORGANISM: homo sapiens
<220> FEATURE:
<221> NAME/KEY: misc_feature
<222> LOCATION: 17, 18
<223> OTHER INFORMATION: N=A, G, T or C
<220> FEATURE:
<221> NAME/KEY: misc_feature
<222> LOCATION: 19
<223> OTHER INFORMATION: S=G or C

<400> SEQUENCE: 10
caacattaaa gacaccnnsa tacactgggt gcgtc                                   35

<210> SEQ ID NO 11
<211> LENGTH: 62
<212> TYPE: DNA
<213> ORGANISM: homo sapiens
<220> FEATURE:
<221> NAME/KEY: misc_feature
<222> LOCATION: 20, 21, 41, 42, 47, 48
<223> OTHER INFORMATION: N=A, G, T or C
<220> FEATURE:
<221> NAME/KEY: misc_feature
<222> LOCATION: 22, 43, 49
<223> OTHER INFORMATION: S=G or C

<400> SEQUENCE: 11
gggcctggaa tgggttgcan nsatttatcc tacgaatggt nnsactnnst atgccgatag        60
cg                                                                      62

<210> SEQ ID NO 12
<211> LENGTH: 34
<212> TYPE: DNA
<213> ORGANISM: homo sapiens
<220> FEATURE:
<221> NAME/KEY: misc_feature
<222> LOCATION: 17, 18
```

<223> OTHER INFORMATION: N=A, G, T or C
<220> FEATURE:
<221> NAME/KEY: misc_feature
<222> LOCATION: 19
<223> OTHER INFORMATION: N=G or C

<400> SEQUENCE: 12
ctattattgt tctagannsg gaggggacgg cttc                          34

<210> SEQ ID NO 13
<211> LENGTH: 35
<212> TYPE: DNA
<213> ORGANISM: homo sapiens
<220> FEATURE:
<221> NAME/KEY: misc_feature
<222> LOCATION: 16, 17
<223> OTHER INFORMATION: N=A, G, T or C
<220> FEATURE:
<221> NAME/KEY: misc_feature
<222> LOCATION: 18
<223> OTHER INFORMATION: S=G or C

<400> SEQUENCE: 13
cagcaacatt atactnnscc tcccacgttc ggaca                         35

<210> SEQ ID NO 14
<211> LENGTH: 81
<212> TYPE: DNA
<213> ORGANISM: homo sapiens
<220> FEATURE:
<221> NAME/KEY: misc_feature
<222> LOCATION: 41, 42, 44, 45, 47, 48, 50, 51, 53, 54
<223> OTHER INFORMATION: N=A, G, T or C
<220> FEATURE:
<221> NAME/KEY: misc_feature
<222> LOCATION: 43, 46, 49, 52, 55
<223> OTHER INFORMATION: S=G or C

<400> SEQUENCE: 14
gcgtgctgag gacactgccg tctattattg ttctagatgg nnsnnsnnsn nsnnstatgc    60
tatggactac tggggtcaag g                                        81

<210> SEQ ID NO 15
<211> LENGTH: 54
<212> TYPE: DNA
<213> ORGANISM: homo sapiens
<220> FEATURE:
<221> NAME/KEY: misc_feature
<222> LOCATION: 16, 17, 28, 29, 34, 35
<223> OTHER INFORMATION: N=A, G, T or C
<220> FEATURE:
<221> NAME/KEY: misc_feature
<222> LOCATION: 18, 30, 36
<223> OTHER INFORMATION: S=G or C

<400> SEQUENCE: 15
ccgaaactac tgattnnstc ggcatccnns ctcnnstctg gagtcccttc tcgc      54

<210> SEQ ID NO 16
<211> LENGTH: 47
<212> TYPE: DNA
<213> ORGANISM: homo sapiens
<220> FEATURE:
<221> NAME/KEY: misc_feature
<222> LOCATION: 15, 16, 30, 31
<223> OTHER INFORMATION: N=A, G, T or C
<220> FEATURE:
<221> NAME/KEY: misc_feature
<222> LOCATION: 17, 32
<223> OTHER INFORMATION: S=G or C

<400> SEQUENCE: 16
ggggagggga cggcnnstat gctatggacn nstggggtca aggaacc     47

<210> SEQ ID NO 17
<211> LENGTH: 43
<212> TYPE: DNA
<213> ORGANISM: homo sapiens

<400> SEQUENCE: 17
tgtaaaacga cggccagtcc gtttaggtgt tttcacgagc act     43

<210> SEQ ID NO 18
<211> LENGTH: 42
<212> TYPE: DNA
<213> ORGANISM: homo sapiens

<400> SEQUENCE: 18
caggaaacag ctatgaccgt tccacgacac cgtcaccggt tc     42

<210> SEQ ID NO 19
<211> LENGTH: 11
<212> TYPE: PRT
<213> ORGANISM: homo sapiens

<400> SEQUENCE: 19

Arg Ala Ser Gln Asp Val Asn Thr Ala Val Ala
 1               5                  10

<210> SEQ ID NO 20
<211> LENGTH: 7
<212> TYPE: PRT
<213> ORGANISM: homo sapiens

<400> SEQUENCE: 20

Ser Ala Ser Phe Leu Tyr Ser
 1               5

<210> SEQ ID NO 21
<211> LENGTH: 9
<212> TYPE: PRT
<213> ORGANISM: homo sapiens

<400> SEQUENCE: 21

Gln Gln His Tyr Thr Thr Pro Pro Thr
 1               5

<210> SEQ ID NO 22
<211> LENGTH: 10
<212> TYPE: PRT
<213> ORGANISM: homo sapiens

<400> SEQUENCE: 22

Gly Phe Asn Ile Lys Asp Thr Tyr Ile His
 1               5                  10

<210> SEQ ID NO 23
<211> LENGTH: 17
<212> TYPE: PRT
<213> ORGANISM: homo sapiens

<400> SEQUENCE: 23

Arg Ile Tyr Pro Thr Asn Gly Tyr Thr Arg Tyr Ala Asp Ser Val Lys
 1               5                  10                  15

Gly

```
<210> SEQ ID NO 24
<211> LENGTH: 11
<212> TYPE: PRT
<213> ORGANISM: homo sapiens

<400> SEQUENCE: 24

Trp Gly Gly Asp Gly Phe Tyr Ala Met Asp Tyr
 1               5                  10
```